United States Patent [19]
Kawai et al.

[11] Patent Number: 5,767,971
[45] Date of Patent: Jun. 16, 1998

[54] APPARATUS FOR MEASURING REFRACTIVE INDEX OF MEDIUM USING LIGHT, DISPLACEMENT MEASURING SYSTEM USING THE SAME APPARATUS, AND DIRECTION-OF-POLARIZATION ROTATING UNIT

[75] Inventors: Hitoshi Kawai, Kawasaki; Jun Kawakami, Yamato; Akira Ishida, Tsuchiura; Kouichi Tsukihara, Ota, all of Japan

[73] Assignee: Nikon Corporation, Japan

[21] Appl. No.: 574,704

[22] Filed: Dec. 19, 1995

[30] Foreign Application Priority Data

| Dec. 30, 1994 | [JP] | Japan | 6-335696 |
| Mar. 20, 1995 | [JP] | Japan | 7-060969 |
| Mar. 24, 1995 | [JP] | Japan | 7-066469 |
| Aug. 21, 1995 | [JP] | Japan | 7-212016 |

[51] Int. Cl.$^6$ ................................ G01B 9/02
[52] U.S. Cl. .................. 356/351; 356/361; 356/349
[58] Field of Search ................ 356/351, 358, 356/349, 364, 361; 359/383, 494, 497, 501

[56] References Cited

U.S. PATENT DOCUMENTS

| 3,399,591 | 9/1968 | Drougard et al. | 356/366 |
| 4,948,254 | 8/1990 | Ishida | 356/351 |
| 5,404,222 | 4/1995 | Lis | 356/351 |

FOREIGN PATENT DOCUMENTS

| 4403021 | 8/1994 | Germany | 356/361 |

Primary Examiner—Samuel A. Turner
Attorney, Agent, or Firm—Pennie & Edmonds LLP

[57] ABSTRACT

A second harmonic generation (SHG) device is used for conversion of wavelength. The direction of polarization of light beams is suitably rotated by a direction-of-polarization rotating unit, for example by 45°, and thereafter these light beams are guided into the SHG device. This can minimize attenuation of intensity of light beam due to conversion of wavelength. Hence, using this direction-of-polarization rotating unit in the apparatus for measuring the medium, the intensity of light being incident upon the photodetector can be increased, whereby the refractive index of the medium can be measured more accurately than by the conventional apparatus.

22 Claims, 21 Drawing Sheets

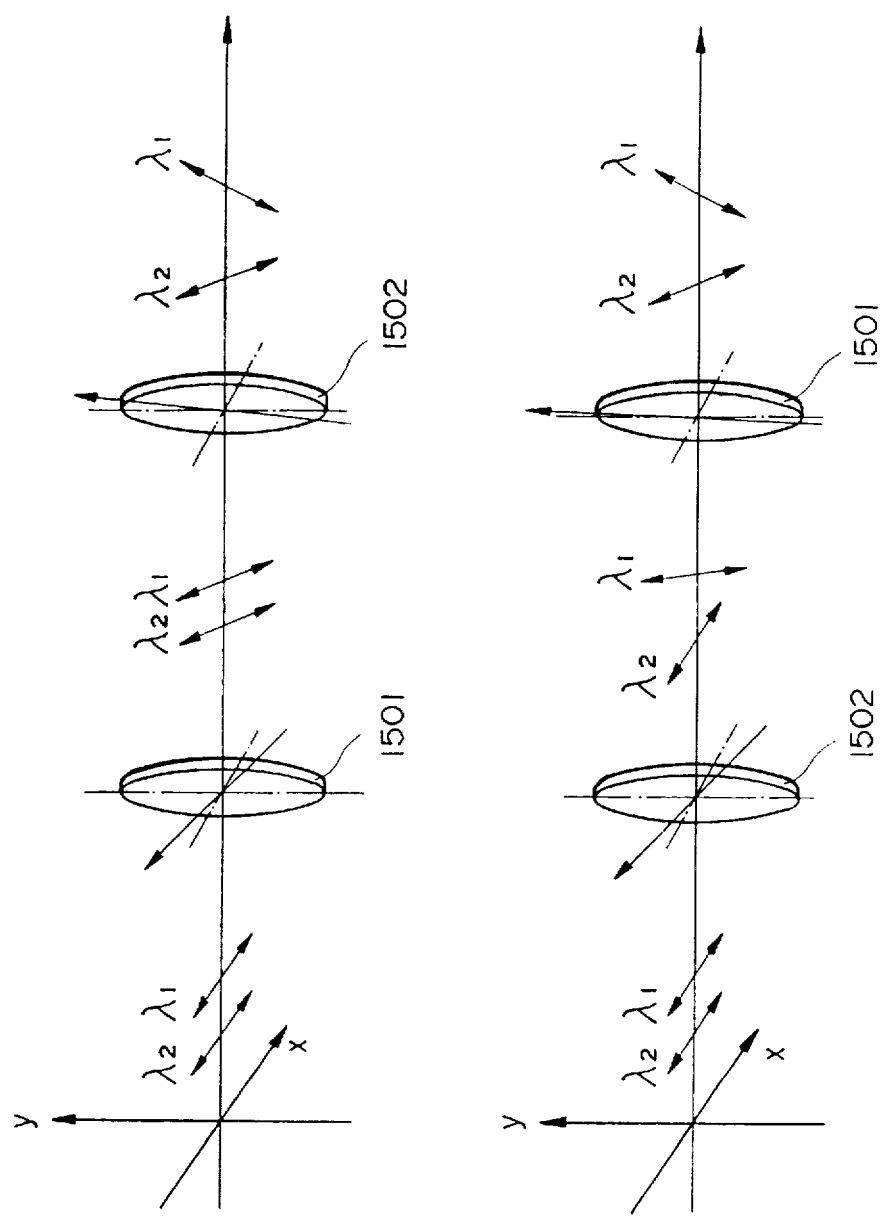

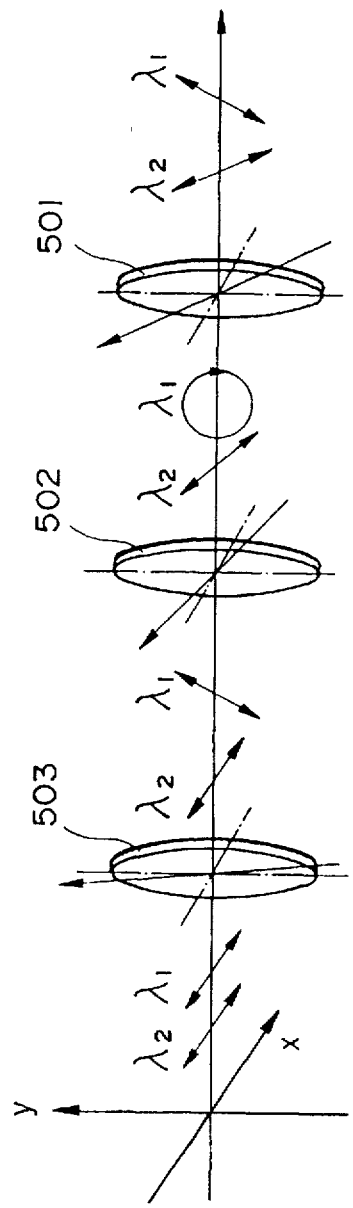
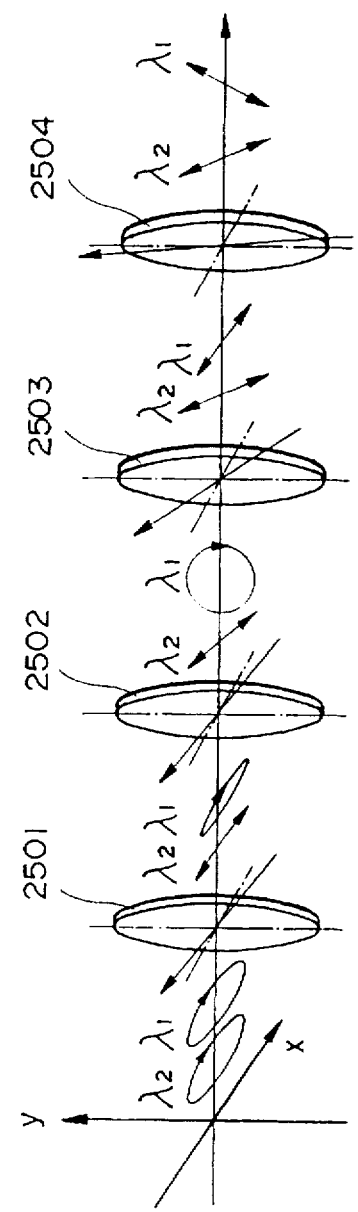
Fig. 30
Fig. 31

APPARATUS FOR MEASURING REFRACTIVE INDEX OF MEDIUM USING LIGHT, DISPLACEMENT MEASURING SYSTEM USING THE SAME APPARATUS, AND DIRECTION-OF-POLARIZATION ROTATING UNIT

BACKGROUND OF THE INVENTION

1. Field of the Invention

The present invention relates to an apparatus for measuring a refractive index of a medium, using light, and a direction-of-polarization rotating unit for rotating the plane of polarization of polarized light used in the same measuring apparatus. Particularly, the present invention is directed to an apparatus for detecting a refractive index of a gas as a medium to be measured, such as the air near an exposure apparatus, and an apparatus for detecting a refractive index of an optical component in the exposure apparatus, as a medium to be measured. The apparatus of the present invention relates to a refractive index change monitor for such media and a light wave interference measuring apparatus for performing high-accuracy displacement measurement.

2. Related Background Art

A conventional distance measuring apparatus is described in U.S. Pat. No. 5,404,222. In this disclosure, the apparatus is arranged to compensate an error due to a change in the refractive index of the air when a distance is measured to an object through the air. Homodyne detection is used for this detection of error. It is difficult for the apparatus as disclosed in the US patent to accurately measure the error, because the intensity is weak of the light measured by a photodetector for measurement of error. Another distance measuring apparatus of this type is described in U.S. Pat. No. 4,948,254. It is also difficult for the distance measuring apparatus disclosed in this patent to accurately measure the error, because the intensity is weak of the light measured by the photodetector for measurement of error.

SUMMARY OF THE INVENTION

In order to accurately measure a refractive index of a medium, using light, it is necessary that the intensity be high of the light received by the photodetector. The photodetector provided in this apparatus measures two light beams passing through a same medium and interfering with each other. The two light beams are linearly polarized light when being incident upon the photodetector. When passing in the medium, frequencies of the respective light beams are different from each other. When detected by the photodetector, frequencies of the respective light beams are equal to each other. The reason is that the wavelength of one light beam is converted into the wavelength of the other light beam before these light beams are incident upon the photodetector. A second harmonic generation (SHG) element is used for this conversion of wavelength. The plane of polarization of the light beam to be wavelength-converted is suitably rotated by a plane-of-polarization rotating unit, for example by 45°, and thereafter these light beams are guided into the SHG device. This can minimize attenuation of intensity of light beam due to conversion of wavelength. Hence, using this plane-of-polarization rotating unit in the apparatus for measuring the medium, the intensity of light being incident upon the photodetector can be increased, whereby the refractive index of the medium can be measured more accurately than by the conventional apparatus. A compact plane-of-polarization rotating unit may be produced by combining three wave plates, but the plane-of-polarization rotating unit of the present invention is by no means limited to it.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 28 to 31 are drawings to show modifications of the direction-of-polarization rotating apparatus.

DESCRIPTION OF THE PREFERRED EMBODIMENTS

Figure 4:
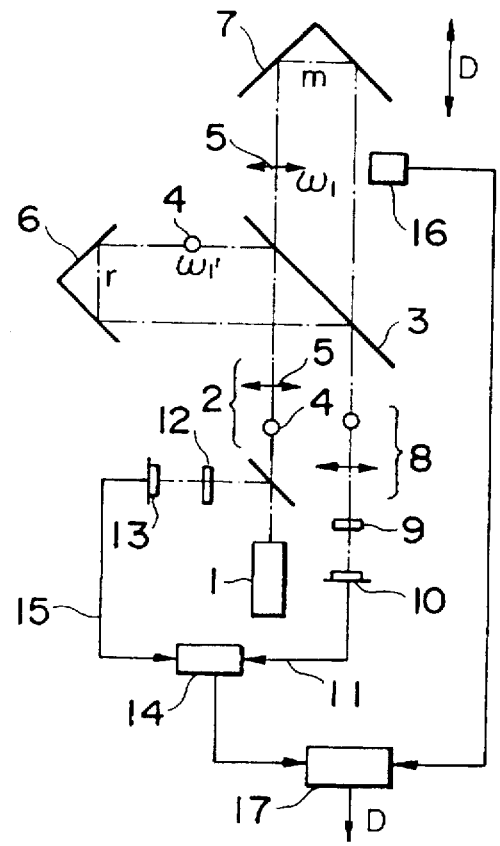
FIG. 4 is a block diagram of an interferometric distance measuring device provided with a function to correct a change in the refractive index of the air, to be compared with the present invention.

First, a light wave interference measuring apparatus, to be compared with the present invention, is briefly explained using FIG. 4.

The light wave interference measuring apparatus of FIG. 4 is an apparatus for measuring a displacement Dm of a moving mirror 7 along the direction of the optical path. A light source 1 emits distance-measuring light 2 including a measuring light 5 of frequency $\omega$ and a reference light 4 of frequency $\omega'$. The measuring light 5 and reference light 4 have respective frequencies slightly different from each other ($\omega' = \omega + \Delta\omega$) and directions of polarization perpendicular to each other. When the distance-measuring light 2 is incident upon a polarization beam splitter 3, the distance measuring light 2 is separated into the reference light ($\omega_1'$) 4 and the measuring light ($\omega_1$) 5. The reference light 4 becomes a reference beam, which is reflected by a stationary mirror 6 and again is incident upon the polarization beam splitter 3. On the other hand, the measuring light 5 becomes a measuring beam, which is reflected by the moving mirror 7 and thereafter returns to the polarization beam splitter 3. Then the measuring light 5 emerges from the polarization beam splitter 3 coaxially with the reference light 4, thus becoming distance-measuring light 8 including the reference light 4 and the measuring beam 5. The distance-measuring light 8 is subjected to polarization interference in a polarizer 9. The interference light is received by a photodetector 10. An interference beat signal (frequency $\Delta\omega$) 11, converted into by the photodetector 10, is then guided into a phase meter 14, and a displacement D ($\omega$) of the moving mirror is obtained by measuring a change in the phase difference relative to a reference signal 15 obtained by preliminarily receiving the beam from the light source immediately after it.

However, in order to preform precise distance measurement by interference of light waves as shown in FIG. 4, a change in the refractive index of the air cannot be ignored. Then an air sensor 16 may be used, as shown in FIG. 4, as means for correcting a distance measurement error due to a change in the refractive index of the air to measure the temperature, the pressure, and the humidity of the air on the optical path of distance measurement, and using a result of this measurement, the apparatus can compensate the error due to the change in the refractive index of the air to vacuum correction.

Namely, supposing a true displacement of a measured object is D, the refractive index of the air is n, and n is spatially uniform, then a displacement Dm measured by the interferometer is expressed as follows.

$$Dm = nD \quad (1)$$

Here, when n is expressed by the wavelength of light, Eq. 1 is written as follows.

$$Dm = (\lambda_0/\lambda)D \quad (2)$$

Here, $\lambda_0$ is the wavelength of light in a vacuum, and $\lambda$ is the wavelength along the optical path of distance measurement.

Since $\lambda$ is a quantity that is determined by the temperature, the pressure, and the humidity of the air, the wavelength $\lambda$ can be calculated by measuring the temperature, the pressure, and the humidity along the optical path by the air sensor 16. Therefore, the true displacement D is obtained using Eq. 2.

This technique is effective when the change is uniform of the refractive index of the air along the optical path of distance measurement, because the detection by the air sensor is carried out only at one point in the optical path of distance measurement. However, correction becomes inaccurate if there are local changes of the air on the optical path of distance measurement. There is a limit in increasing the number of air sensors on the optical path of distance measurement to monitor the temperature, the pressure, and the humidity at each of many points, and the cost also increases for increasing the number of air sensors.

Apparatus according to the embodiments as described below can accurately correct an error of distance measurement due to the change in the refractive index even if a local environment is present upon measurement. Brief description of the apparatus according to the embodiments as described below is first given.

This apparatus has means for using first light of frequency $\omega_1$ to detect a displacement $D(\omega_1)$ of a measured object, means for using second light of frequency $\omega_2$ and third light of frequency $\omega_3$, which are different in frequency from the first light of frequency $\omega_1$, to detect a difference $\{D(\omega_3) -D(\omega_2)\}$ between $D(\omega_3)$ corresponding to a displacement of the measured object when detected with the third light and $D(\omega_2)$ corresponding to a displacement of the measured object when detected with the second light, and means for using the detection results $D(\omega_1)$ and $\{D(\omega_3) -D(\omega_2)\}$ and the following Eq. 3 to calculate a true displacement D of the measured object.

$$D=D(\omega_1)-\{F(\omega_1)/\{F(\omega_3)-F(\omega_2)\}\}\cdot\{D(\omega_3)-D(\omega_2)\} \quad (3)$$

Here, F represents a function preliminarily obtained, which is dependent on the frequency of light.

The refractive index n of the air is expressed as follows where N is the density of the air and $F(\omega)$ is a function determined only by the frequency of light independently of the density of the air if the composition ratio of the air is constant.

$$n=1+N\cdot F(\omega) \quad (4)$$

Thus, path lengths between two points A and B (FIG. 1) for respective light beams of three frequencies are given as follows.

$$D(\omega_1) = \int_A^B n(x,\omega_1)-dx = \int_A^B \{1+N(x)-F(\omega_1)\}dx \quad \text{(Eq. 5)}$$

$$D(\omega_2) = \int_A^B n(x,\omega_2)-dx = \int_A^B \{1+N(x)-F(\omega_2)\}dx \quad \text{(Eq. 6)}$$

$$D(\omega_3) = \int_A^B n(x,\omega_3)-dx = \int_A^B \{1+N(x)-F(\omega_3)\}dx \quad \text{(Eq. 7)}$$

From Eqs. 6 and 7, the following equation is attained.

$$\int_A^B N(x)dx = \frac{D(\omega_3)-D(\omega_2)}{F(\omega_3)-F(\omega_2)} \quad \text{(Eq. 8)}$$

Substituting it into Eq. 5, the true displacement D between points A and B can be obtained from the following equation.

$$D = \int_A^B dx = D(\omega_1) - \frac{F(\omega_1)}{F(\omega_3)-F(\omega_2)}\{D(\omega_3)-D(\omega_2)\} \quad \text{(Eq. 9)}$$

The present apparatus is provided with means for detecting each of $D(\omega_1)$ and $D(\omega_3)-D(\omega_2)$ in Eq. 9, and obtains the true displacement by calculating Eq. 9, based on the detection results.

Figure 1:
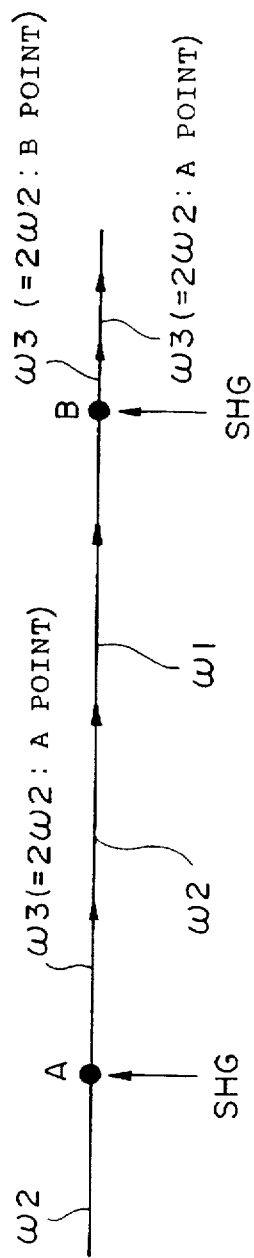
FIG. 1 is an explanatory drawing to show a principle of the refractive index change measuring apparatus of the present invention.

For example, $D(\omega_1)$ may be obtained by an interference optical system. Further, $D(\omega_3)-D(\omega_2)$ may be obtained utilizing second harmonic generation (SHG). In detail, as shown in FIG. 1, a part of light of frequency $\omega_2$ is converted into the light of frequency $\omega_3$ (frequency $\omega_3=2\omega_2$) at point A, and the light of frequency $\omega_3$ is let to travel between point A and point B coaxially with the light of $\omega_2$, and further the light of frequency $\omega_2$ is converted into the light of frequency $\omega_3$ at point B, thereby the light of frequency $\omega_3$ at point B interfere with the light frequency $\omega_3$ at point A to obtain a difference $D(\omega_3)-D(\omega_2)$ between the optical path length along points AB for $\omega_3$ and the optical path length along points AB for $\omega_2$. Thus, the true displacement can be calculated using Eq. 9 from an output from the interference optical system and an interference output between the two light of frequencies $\omega_2$ and $\omega_3$ ($=2\omega_2$).

The embodiments of the present invention are now explained with reference to the drawings. In the description, same reference numerals denote same elements, and redundant description will be omitted.

Figure 2:
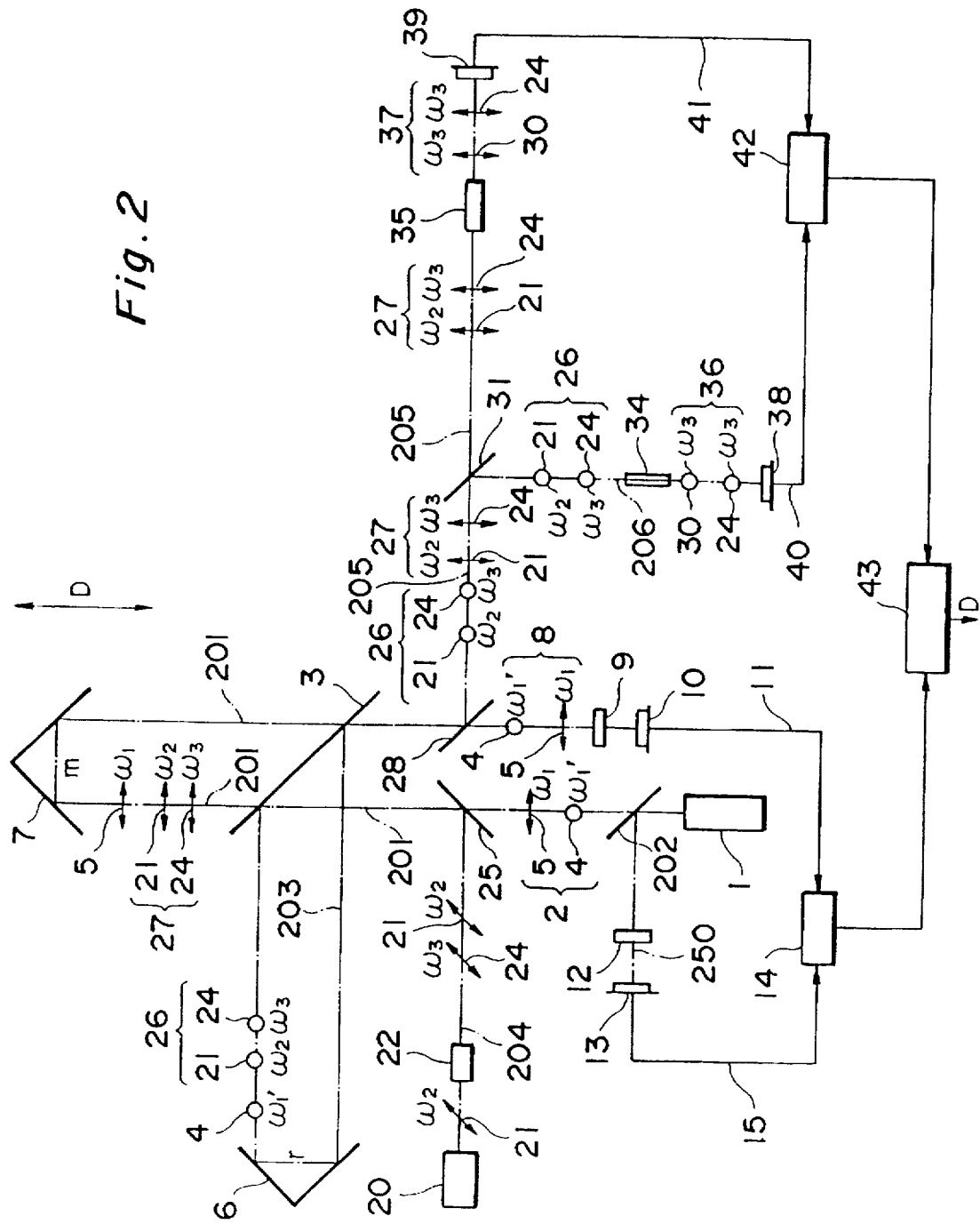
FIG. 2 is a block diagram of a light wave interference measuring apparatus according to a first embodiment of the present invention.

First explained referring to FIG. 2 is the light wave interference measuring apparatus of the first embodiment according to the present invention.

The light wave interference measuring apparatus of FIG. 2 monitors an change in the refractive index of the air by the homodyne interferometry.

First explained is a configuration of the light wave interference measuring apparatus of FIG. 2.

Disposed on an optical path 201 in the following order are a light source 1, a beam splitter 202, an dichroic mirror 25, a polarization beam splitter 3, a moving mirror 7 a displacement of which is to be measured, an dichroic mirror 28, a polarizer 9, and a photodetector 10. A stationary mirror 6 is disposed on an optical path 203 of light reflected by the polarization beam splitter 3. Further, a polarizer 12 and a photodetector 13 are disposed on an optical path 250 of light reflected by the beam splitter 202. The light source 1 emits distance-measuring light 2 including measuring light 5 of frequency $\omega_1$ and reference light 4 of frequency $\omega_1'$. Specifically, the light source 1 is a He-Ne laser, and the measuring light 5 is of the wavelength 633 nm. The measuring light 5 and the reference light 4 have respective frequencies slightly different from each other ($\omega_1'=\omega_1+\Delta\omega$) and directions of polarization perpendicular to each other. The photodetector 10 and photodetector 13 are connected to a phase meter 14. These compose an optical system for obtaining a displacement $D(\omega_1)$ of the moving mirror 7, measured with the light of frequency $\omega_1$.

Further disposed on an optical path 204 are a light source 20 and a second harmonic generation device (hereinafter referred to as an SHG device) 22. The optical path 204 is coupled with the optical path 201 through the dichroic mirror 25. The light source 20 emits light 21 of frequency $\omega_2$. The SHG device 22 converts part of the light 21 into light 24 of frequency $\omega_3=2\omega_2$. Specifically, the light source 20 is a YAG laser, which emits light of wavelength 1064 nm. The SHG device 22 is formed of a nonlinear optical material KTiOPO$_4$. Further, a polarization beam splitter 31, an SHG device 35, and a photodetector 39 are disposed on an optical path 205 separated from the optical path 201 by the dichroic mirror 28. An SHG device 34 and a photodetector 38 are disposed on an optical path 206 separated from the optical path 205 by the polarization beam splitter 31. The SHG devices 34, 35 are made of the same material as the SHG device 22 is. The photodetectors 38, 39 are connected to a phase meter 42. These constitute together with the polarization beam splitter 3, stationary mirror 6, and moving mirror 7 an optical system for obtaining the change in the phase difference between the displacement $D(\omega_3)$ of the moving mirror 7 measured with the light of frequency $\omega_3$ and the displacement $D(\omega_2)$ of the moving mirror 7 measured with the light of frequency $\omega_2$. This optical system is one for monitoring a change in the refractive index of the air by obtaining $D(\omega_3)-D(\omega_2)$ by the homodyne interferometry.

The phase meter 14 and phase meter 42 are connected to an calculator 43. The calculator 43 executes the calculation to obtain the true displacement D of the moving mirror 7 and the calculation to obtain a refractive index $n(\omega_1)$ of a medium in the optical path for the light of frequency $\omega_1$.

Next explained is the operation for measuring the true displacement D of the moving mirror 7 as eliminating influence of the change in the refractive index of the air by this apparatus.

First, the distance-measuring light 2, including the reference light 4 and the measuring light 5 emitted from the light source 1 with the slightly different frequencies and directions of polarization perpendicular to each other, is incident into the polarization beam splitter 3 to be split into the reference light ($\omega_1'$) 4 becoming the reference light and the measuring light ($\omega_1$) 5 becoming the measuring light. The reference light 4 is reflected by the stationary mirror 6 and thereafter is incident again into the polarization beam splitter 3. On the other hand, the measuring light 5 is reflected by the moving mirror 7, which is an object to be measured, and thereafter returns to the polarization beam splitter 3 then to emerge from the polarization beam splitter 3 coaxially with the reference light.

The distance-measuring light 8 including the reference light 4 and the measuring light 5, emerging from the polarization beam splitter 3, then passes the polarizer 9. Passing through the polarizer 9, the reference light 4 and measuring light 5 interfere with each other. Information of interference fringes is converted into an electric signal by the photodetector 10. An interference beat signal (frequency $\Delta\omega$) 11 converted into by the photodetector 10, and a reference signal 15 obtained by preliminarily receiving the light immediately after the light source are input into the phase meter 14 to measure a change $\delta_1$ of the phase difference of the interference beat signal 11 relative to the phase of the reference signal 15 by the heterodyne interferometry.

On the other hand, the light 21 of frequency $\omega_2$ emitted from the light source 20 is incident into the SHG (second harmonic generation) device 22 to produce light 24 of frequency $\omega_3$ ($=2\omega_2$). Beams of the light 21 and the light 24 are beams of linearly polarized light having directions of polarization making respective angles of 45 degrees relative to the measuring light 5 and reference light 4 as described above. The dichroic mirror 25 couples the two beams of the respective wavelengths, i.e., the light 21 of frequency $\omega_2$ transmitted by the SHG device 22 and the light 24 of frequency $\omega_3$, with the distance-measuring light 2 as described above, and the coupled light is incident into the polarization beam splitter 3. The light 21 and light 24 of the two frequencies (wavelengths) incident into the polarization beam splitter 3 is separated into reference light 26 having the same direction of polarization as the reference light 4 and measuring light 27 having the same direction of polarization as the measuring light 5. Each of the reference light 26 and the measuring light 27 includes the light 21 of frequency $\omega_2$ and the light 24 of frequency $\omega_3$. Then the reference light 26 is reflected by the stationary mirror 6, and the measuring light 27 is reflected by the moving mirror 7. After that, they coaxially emerge from the polarization beam splitter 3.

The light including the two frequencies emerging from the polarization beam splitter 3 is separated from the distance-measuring light 8 by the dichroic mirror 28. Further, the polarization beam splitter 31 separates the light 26 including the two frequencies, having passed through the reference optical path, from the light 27 including the two frequencies, having passed through the measuring optical path. The light 26 or 27 is incident into the SHG device 34 or 35, respectively. In each SHG device 34, 35, the second harmonic wave appears from the light 21 of the smaller frequency $\omega_2$ out of the light of the two frequencies, thus each element producing light 30 of frequency $\omega_3$ ($=2\omega_2$). The light 30 interferes with the light 24 of the larger frequency, having passed through the SHG device 34, 35. Interference light 36, 37 is received by the photodetector 38, 39, respectively. An interference signal 40 from the interference light 36 between the light beams including the two frequencies, having passed through the reference optical path, and an interference signal 41 from the interference light 37 between the light beams including the two frequencies, having passed through the measuring optical path, are input into the phase meter 42, which measures a change in the phase difference of the interference signal 41 relative to the phase of the interference signal 40 to detect a phase difference $\delta_2$.

An output from the phase meter 14 of the light wave interference measuring apparatus, and an output from the phase meter 42 input into the calculator 43. The calculator 43 obtains the displacement $D(\omega_1)$ of the moving mirror 7 by calculation with the change in the phase difference $\delta_1$ and wavelength $\omega_1$. Specifically, the displacement is obtained by the following equation.

$$D(\omega_1)=\delta_1 \times (c/\omega_1) \times (\tfrac{1}{2})$$

Here, c is the velocity of light.

Further, the equation obtains $D(\omega_3)-D(\omega_2)$ by calculation with the phase difference $\delta_2$ output from the phase meter 42 and the frequency $\omega_3$. Specifically, it is obtained by the following equation.

$$D(\omega_3)=D(\omega_2)=\delta_2 \times (c/\omega_3) \times (\tfrac{1}{2})$$

Here, c represents the velocity of light.

Further, the calculator 43 executes the following calculation for correcting the change in the refractive index of the air to obtain the true displacement D of the moving mirror 7.

$$D=D(\omega_1)=[F(\omega_1)/\{F(\omega_3)-F(\omega_2)\}]\cdot\{D(\omega_3)-D(\omega_2)\} \qquad (10)$$

Here, $F(\omega_1)/(F(\omega_3)-F(\omega_2))$ is a constant preliminarily obtained by calculation.

The calculator 43 further executes the following calculation with the true displacement D thus obtained and $D(\omega_1)$ to obtain the present refractive index $n(\omega_1)$ of the medium in the optical path for the light of frequency $\omega_1$.

$$n(\omega_1)=D(\omega_1)/D$$

As described above, the light wave interference measuring apparatus of the first embodiment can obtain the true displacement D of the moving mirror 7 and the present refractive index $n(\omega_1)$ of the medium in the optical path for the light of frequency $\omega_1$.

Figure 3:
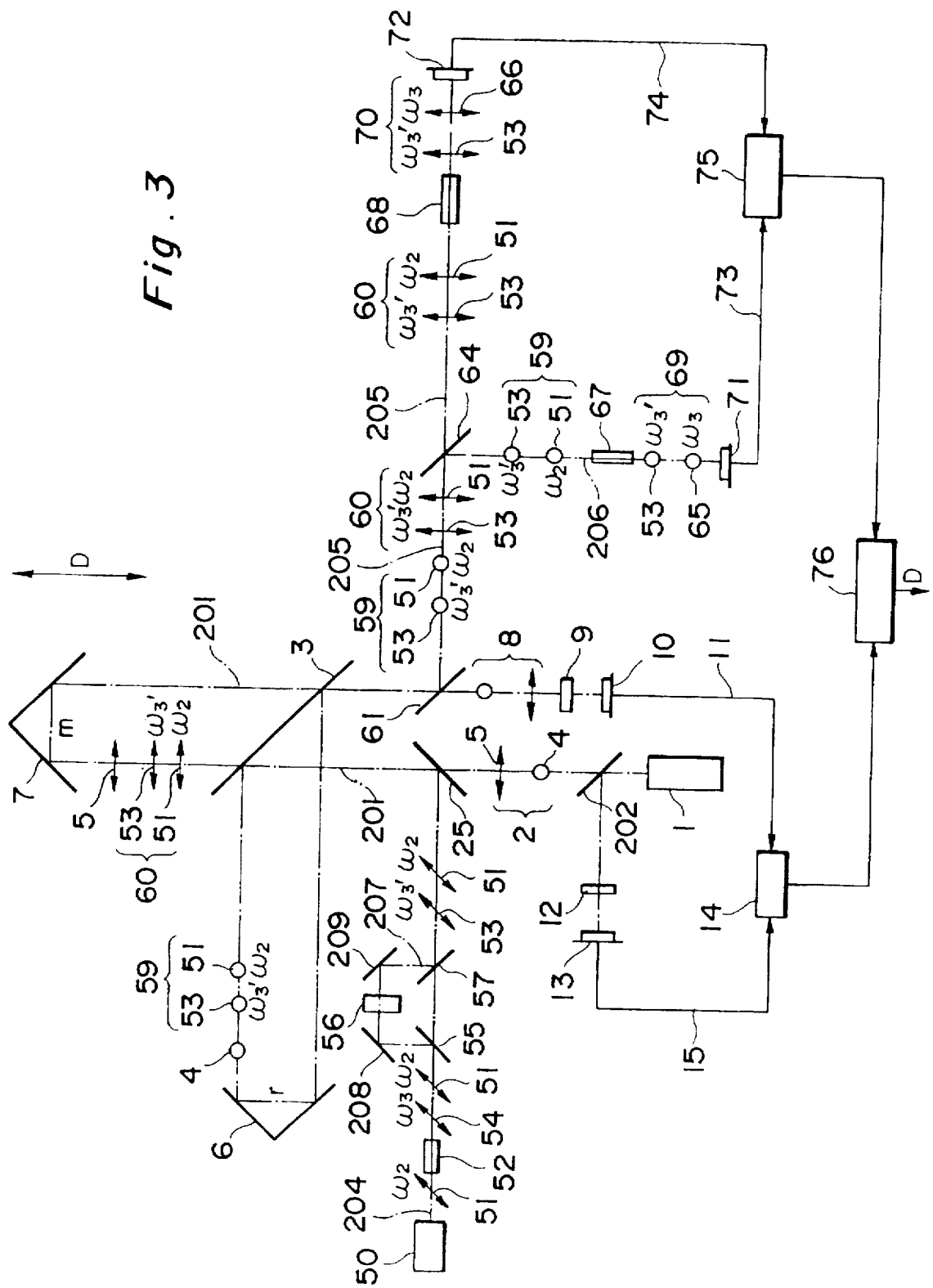
FIG. 3 is a block diagram of another light wave interference measuring apparatus according to a second embodiment of the present invention.

Next explained referring to FIG. 3 is another light wave interference measuring apparatus for monitoring the change in the refractive index of the air by the heterodyne interferometry in the second embodiment of the present invention.

In the measuring apparatus of the present embodiment the optical system for obtaining the displacement $D(\omega_1)$ of the moving mirror 7, measured with the light of wavelength $\omega_1$, is the same as in the first embodiment, as shown in FIG. 3, and thus the description thereof is omitted herein.

The optical system for monitoring the change in the refractive index of the air, by obtaining the difference $\{D(\omega_3)-D(\omega_2)\}$ between the displacement D ($\omega_3$) of the moving mirror 7, measured with the light of frequency $\omega_3$, and the displacement $D(\omega_2)$ of the moving mirror 7, measured with the light of frequency $\omega_2$, is constructed as an optical system of the heterodyne interferometry.

In detail, a light source 50, an SHG device 52, and dichroic mirrors 55, 57 are disposed on the optical path 204.

The optical path 204 is coupled with the optical path 201 through an dichroic mirror 25. A mirror 208, a frequency shifter 56, and a mirror 209 are disposed on an optical path 207 of light reflected by the dichroic mirror 55. The frequency shifter 56 is constructed of an acoustooptic modulator. The optical path 207 is again coupled with the optical path 204 by the dichroic mirror 57. The light source 50 is the same light source as the light source 20 in the first embodiment, which emits light 51 of frequency $\omega_2$. The SHG device 52 is the same material as the SHG device 22 in the first embodiment, which converts part of the light 51 into light 54 of frequency $\omega_3 = 2\omega_2$.

A polarization beam splitter 64, an SHG device 68, and a photodetector 72 are disposed on the optical path 205 separated from the optical path 201 by an dichroic mirror 61. An SHG device 67 and a photodetector 71 are disposed on the optical path 206 separated from the optical path 205 by the polarization beam splitter 64. The SHG devices 67, 68 are formed of the same material as the SHG device 52 is. The photodetectors 71, 72 are connected to a phase meter 75. These constitute together with the polarization beam splitter 3, stationary mirror 6, and moving mirror 7 an optical system for obtaining the change in the phase difference between the displacement $D(\omega_3)$ of the moving mirror 7, measured with the light of frequency $\omega_3$, and the displacement $D(\omega_2)$ of the moving mirror 7, measured with the light of frequency $\omega_2$.

Next explained is the operation for measuring the true displacement $D(\omega_1)$ of the moving mirror 7 as eliminating influence of the change in the refractive index of the air by this apparatus.

Similarly as in the first embodiment, the phase meter 14 measures a change $\delta_1$ of the phase of the interference beat signal 11 relative to the phase of the reference signal 15 by the heterodyne interferometry.

On the other hand, the light 51 of frequency $\omega_2$ emitted from the light source 50 has the direction of polarization making an angle of 45 degrees with the reference light 4 and measuring light 5. The light 51 of frequency $\omega_2$ is incident into the SHG (second harmonic generation) device 52 to produce light 54 of frequency $\omega_3$ (=$2\omega_2$). The light 54 of frequency $\omega_3$ emerging from the SHG device is separated by the dichroic mirror 55 from the light 51 of frequency $\omega_2$, having passed through the SHG device 52. Further, the light 54 of frequency $\omega_3$ (=$2\omega_2$) comes to have a frequency slightly shifted by the frequency shifter 56 to become light 53 of frequency $\omega_3' = \omega_3 + \Delta\omega'$. The light 53 of $\omega_3'$ is again combined with the light 51 of frequency $\omega_2$ by the dichroic mirror 57, and the combined light is further combined in the distance-measuring light 2 by the dichroic mirror 25 to be incident upon the polarization beam splitter 3.

The light including the two frequencies being incident upon the polarization beam splitter 3 is split into reference light 59 and measuring light 60, which are reflected by the stationary mirror 6 and by the moving mirror 7, respectively, in the same manner as the reference light 4 and measuring light 5, thereafter to coaxially emerge from the polarization beam splitter 3.

The light including the two frequencies, emerging from the polarization beam splitter 3, is separated from the distance-measuring light 8 by the optical separating element 61. The light 59, 60 thus separated is then split by the polarization beam splitter 64 into the light 59 having passed through the reference optical path and the light 60 having passed through the measuring optical path to be incident upon the SHG devices 67, 68, respectively. In the SHG device 67, 68 the light 51 of the smaller frequency $\omega$2 out of the light of the two frequencies is converted to SHG conversion to produce light 65, 66, respectively, of frequency $\omega_3$ ($2\omega_2$) of the second harmonic wave. The light 53 passes through the SHG device 67, 68. As explained, the second harmonic wave of the light 51 appears in the SHG device 67, 68. On the other hand, the light 53 is also transmitted as it is. The light 65, 66 (frequency $\omega_3$) heterodyne interferometry with the light 53 (frequency $\omega_3'$) transmitted by the SHG device 67, 68 to form interference fringes. Interference light 69, 70 is received by the photodetector 71, 72, respectively, which converts information of the interference fringes into an electric signal. An interference beat signal 73 from the photodetector 71 and an interference beat signal 74 from the photodetector 72 are input into the phase meter 75, which relatively measures a change in the phase of the interference signal 74 relative to the phase difference of the interference beat signal 73 to obtain a change in the phase difference $\delta_3$.

An output from the phase meter 14 and an output from the phase meter 75 are input into the calculator 76. The calculator 76 obtains the displacement $D(\omega_1)$ of the moving mirror 7 in the same manner as in the first embodiment, by calculation with the change in the phase difference $\delta_1$ and frequency $\omega_1$. Further, the calculator 76 obtains $D(\omega_3') - D(\omega_2)$ by calculation with the change in the phase difference $\delta_3$ output from the phase meter 75 and the frequency $\omega_3'$. Specifically, it is obtained as follows.

$$D(\omega_3') - D(\omega_2) = \delta_3 \times (c/\omega_3') \times (\tfrac{1}{2})$$

Here, c represents the velocity of light.

Further, the calculator 76 executes calculation to correct the change in the refractive index of the air by the following equation to obtain the true displacement D of the moving mirror 7.

$$D = D(\omega_1) - \{F(\omega_1)/\{F(\omega_3') - F(\omega_2)\}\}\cdot \{D(\omega_3') - D(\omega_2)\} \qquad (11)$$

Here, $F(\omega_1)/(F(\omega_3') - F(\omega_2))$ is a constant preliminarily obtained by calculation.

Further, the calculator 76 performs the following calculation with the true displacement D thus obtained and $D(\omega_1)$, thereby obtaining the current refractive index $n(\omega_1)$ of the medium in the optical path for the light of frequency $\omega_1$.

$$n(\omega_1) = D(\omega_1)/D$$

As explained, the light wave interference measuring apparatus of the second embodiment can obtain the true displacement D of the moving mirror 7 and the present refractive index $n(\omega_1)$ of the medium in the optical path for the light of frequency $\omega_1$.

In the first and second embodiments, the true displacement can be detected as correcting the change in the refractive index using Eq. 11 by measuring the displacement of the measured object $D(\omega_1)$, and $\{D(\omega_3) - D(\omega_2)\}$ or $\{D(\omega_3') - D(\omega_2)\}$ with the light of three frequencies $\omega_1$, $\omega_2$, $\omega_3$. The refractive index upon measurement can also be attained at the real time.

Since the second embodiment is arranged to obtain the phase difference by utilizing the heterodyne interferometry for $D(\omega_3') - D(\omega_2)$, it is unlikely to be affected by an error due to an instability of output from the light source 50, and the phase difference can be detected accurately. The detection accuracy of the true displacement D can be thus improved because $D(\omega_3') - D(\omega_2)$ for correction can accurately be detected.

In the first and second embodiments, the optical path of the optical system of $D(\omega_3)$–$D(\omega_2)$ or $D(\omega_3')$–$D(\omega_2)$ for correction is made coincident with the optical path of the optical system for measuring $D(\omega_1)$. Since $D(\omega_3)$–$D(\omega_2)$ or $D(\omega_3')$–$D(\omega_2)$ is a measured value including the change in the refractive index of the air of the entire optical path coincident with the optical path of $D(\omega_1)$, a local index change in the air can be corrected for accurately.

It is to be desired in the light wave interference measuring apparatus of the present embodiment to keep the change in the refractive index of the entire optical path excluding the optical path of the displacing portion of the moving mirror as small as possible in order to measure the change in the refractive index more accurately. For this purpose, the entire optical path except for the optical path of the displacing portion of the moving mirror may be covered by a tube, or the optical system may be arranged to minimize the path-length of the optical path except for the optical path of the displacing portion of the moving mirror, which permits the change in the refractive index to be measured more accurately.

The first and second embodiments employ, as an optical system for detecting $D(\omega_3)$–$D(\omega_2)$ or $D(\omega_3')$–$D(\omega_2)$ for correction, such an arrangement that two light beams with a large wavelength difference are let to travel so as to cause a phase difference due to the index change of the air between the two light beams and thereafter frequency conversion is effected to cause interference. The reason why this arrangement is employed is that there is a feature that the larger the wavelength difference, the greater the phase difference between the two light beams due to the change in the refractive index of the air and on the other hand, that the smaller the frequency difference, the more accurate the detection of the phase difference by interference. This permits the present embodiment to detect the change in the refractive index of the air with accuracy.

Figure 13:
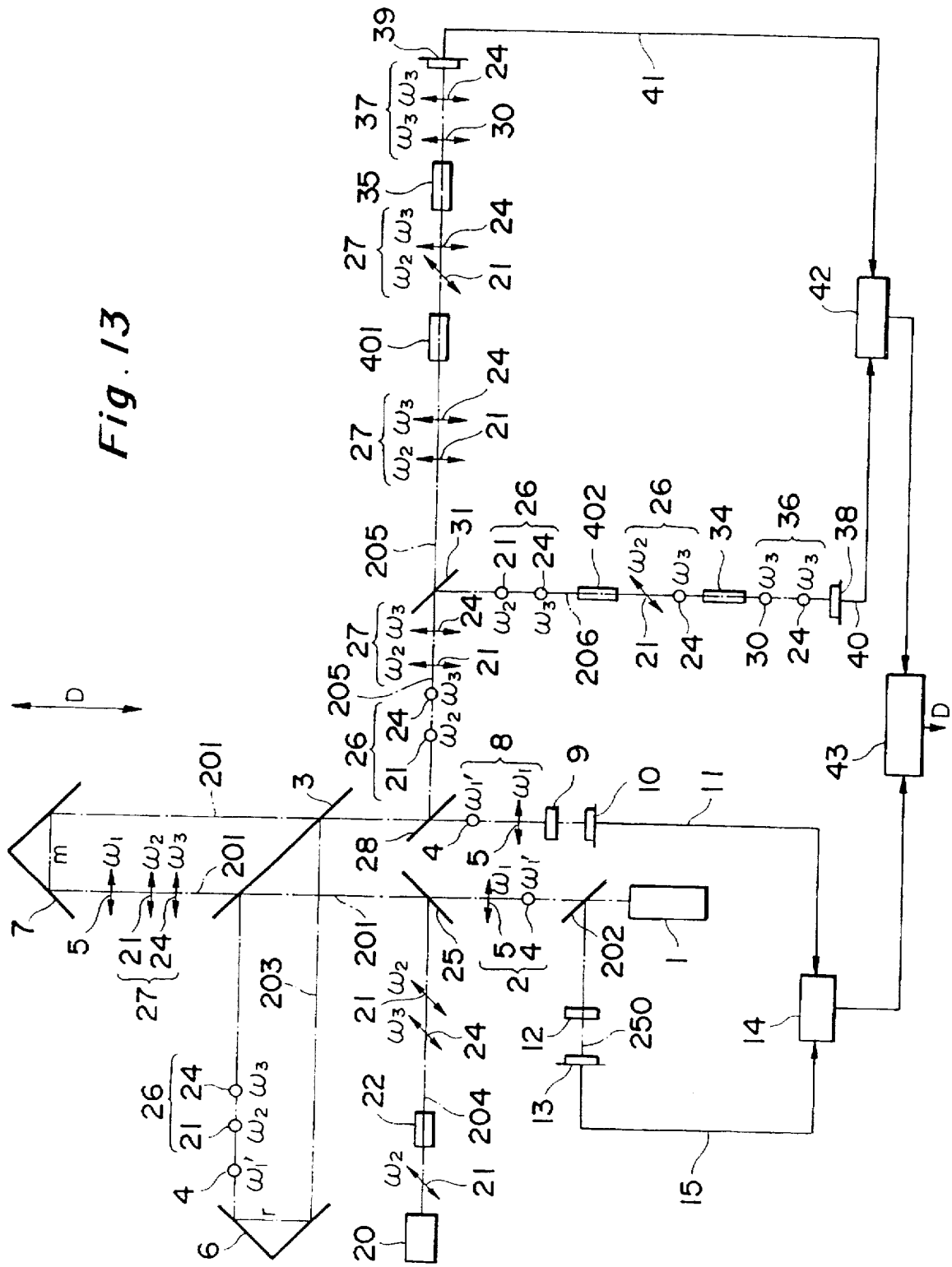
FIG. 13 is a block diagram of a light wave interference measuring apparatus according to a third embodiment of the present invention.

Next explained referring to FIG. 13 is the third embodiment of the present invention, which is the light wave interference measuring apparatus provided with direction-of-polarization rotating apparatus in the optical path.

The light wave interference measuring apparatus of the present embodiment is constructed substantially in the same manner as that of the first embodiment except that the apparatus of the present embodiment has the direction-of-polarization rotating apparatus 401, 402 in the optical axes 205, 206.

The direction-of-polarization rotating apparatus 401 is disposed between the polarization beam splitter 31 and the SHG device 35. The direction-of-polarization rotating apparatus 402 is disposed between the polarization beam splitter 31 and the SHG device 34.

The direction-of-polarization rotating apparatus 402 rotates the direction of polarization of the light 21 of frequency $\omega_2$ included in the reference light 26 to a predetermined direction of polarization. This predetermined direction of polarization is one determined by phase matching conditions of $KTiOPO_4$ crystal for the SHG device 34, and the direction of polarization of the light 21 is rotated to the direction of polarization near 45° relative to the extraordinary direction of the $KTiOPO_4$ crystal in the present embodiment. Further, the direction of polarization of the light 24 of frequency $\omega_3$ is rotated to the extraordinary direction of the $KTiOPO_4$ crystal for the SHG device 34.

Further, the direction-of-polarization rotating apparatus 401 also rotates the direction of polarization of the light 21 of frequency $\omega_2$ included in the measuring light 27 similarly to a predetermined direction of polarization. This predetermined direction of polarization is one determined by phase matching conditions of the $KTiOPO_4$ crystal for the SHG device 35, and the direction of polarization of the light 21 is rotated to the direction of polarization near 45° relative to the extraordinary direction of the $KTiOPO_4$ crystal in the present embodiment. Further, the direction of polarization of the light 24 of frequency $\omega_3$ is rotated to the extraordinary direction of the $KTiOPO_4$ crystal for the SHG device 35.

The $KTiOPO_4$ crystal for the SHG devices 34, 35 has such a property that when the light of frequency $\omega_2$ is incident in the above-described direction of polarization determined from the phase matching conditions (near 45° relative to the extraordinary direction), it efficiently generates the second harmonic wave to emit it as linearly polarized light parallel to the extraordinary direction of crystal. The $KTiOPO_4$ crystal transmits the light of frequency $\omega_3$ incident in the extraordinary direction of crystal without changing the direction of polarization to emit it along the extraordinary direction of the crystal.

Thus, the SHG device 34, 35 each produces the light 30 of frequency $\omega_3$ (=$2\omega_2$), which is the second harmonic wave of the light 21 of the smaller frequency $\omega_2$. Since the light 30 has the same direction of polarization (the extraordinary direction of the $KTiOPO_4$ crystal) as that of the light 24 of the larger frequency, having passed without change through the SHG device 34, 35, they interfere with each other. Interference light 36, 37 is received by a photodetector 38, 39, respectively. Since the other operation is the same as in the first embodiment, the description thereof is omitted herein.

Figure 14:
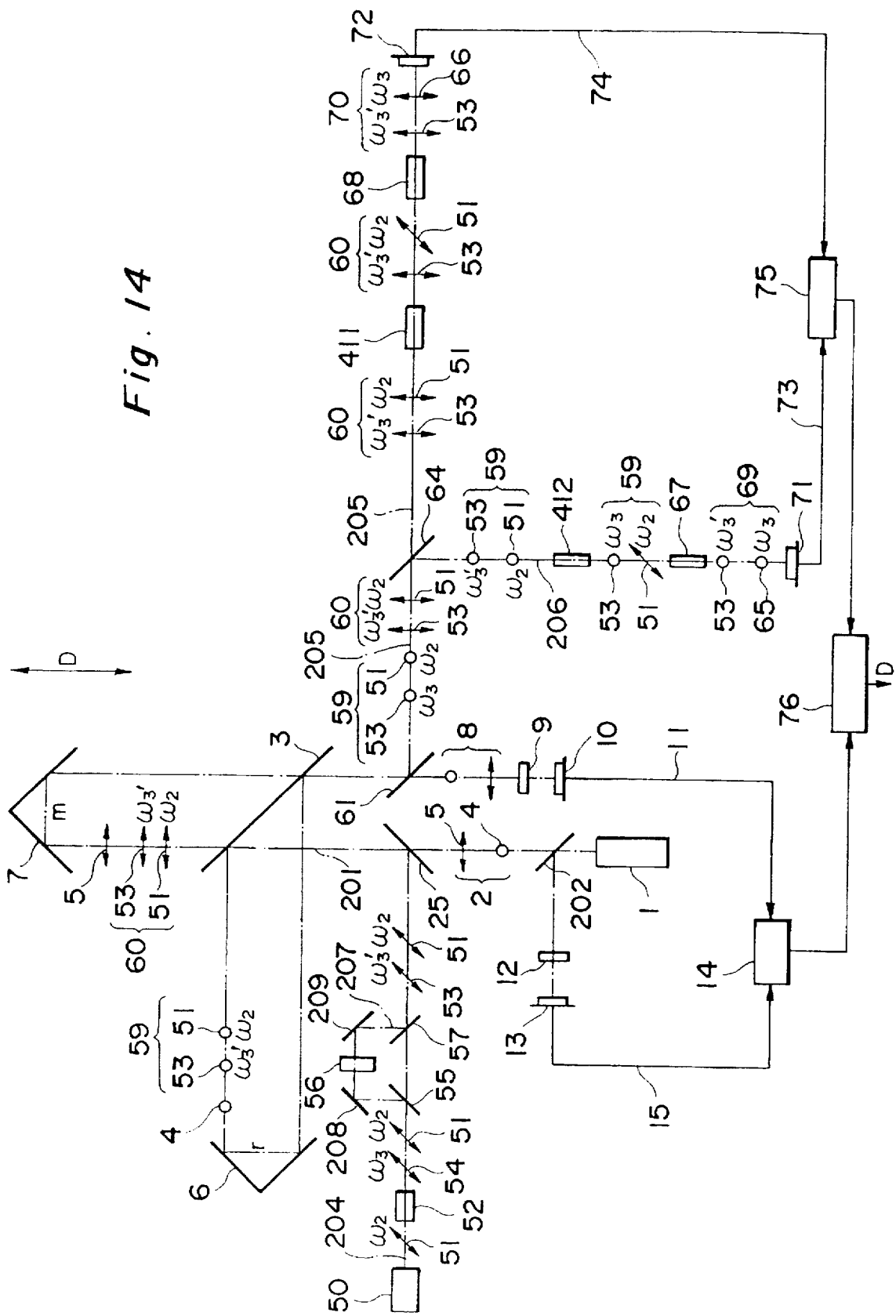
FIG. 14 is a block diagram of another light wave interference measuring apparatus according to a fourth embodiment of the present invention.

Next explained as the fourth embodiment of the present invention referring to FIG. 14 is the light wave interference measuring apparatus provided with direction-of-polarization rotating apparatus 411, 412 in the optical path.

The light wave interference measuring apparatus of the present embodiment is constructed substantially in the same arrangement as that of the second embodiment except that the apparatus of the present embodiment is provided with the direction-of-polarization rotating apparatus in the optical axes 205 and 206.

The direction-of-polarization rotating apparatus 411 is disposed between the polarization beam splitter 64 and the SHG device 68. Further, the direction-of-polarization rotating apparatus 412 is disposed between the polarization beam splitter 64 and the SHG device 67.

The direction-of-polarization rotating apparatus 412 rotates the direction of polarization of the light 51 of frequency $\omega_2$ included in the reference light 59 to a predetermined direction of polarization. This predetermined direction of polarization is one determined by the phase matching conditions of the $KTiOPO_4$ crystal for the SHG device 67, and the direction of polarization of the light 51 is rotated to the direction of polarization near 45° relative to the extraordinary direction of the $KTiOPO_4$ crystal in the present embodiment. Further, the direction of polarization of the light 53 of frequency $\omega_3'$ is rotated to the extraordinary direction of the $KTiOPO_4$ crystal for the SHG device 67.

The direction-of-polarization rotating apparatus 411 also rotates the direction of polarization of the light 51 of frequency $\omega_2$ included in the measuring light 60 similarly to a predetermined direction of polarization. This predetermined direction of polarization is one determined by the phase matching conditions of the $KTiOPO_4$ crystal for the SHG device 68, and the direction of polarization of the light 51 is rotated to the direction of polarization near 45° relative to the extraordinary direction of the $KTiOPO_4$ crystal in the present embodiment. The direction of polarization of the light 53 of frequency $\omega_3'$ is rotated to the extraordinary direction of the KTiOPO$_4$ crystal for the SHG device 68.

The KTiOPO$_4$ crystal for the SHG devices 67, 68 has such a property that when the light of frequency $\omega_2$ is incident in the above-described direction of polarization determined from the phase matching conditions (near 45° relative to the extraordinary direction), it efficiently generates the second harmonic wave to emit it as linearly polarized light parallel to the extraordinary direction of crystal. The KTiOPO$_4$ crystal transmits the light of frequency $\omega_3'$ incident in the extraordinary direction of crystal without changing the direction of polarization to emit it along the extraordinary direction of the crystal.

Thus, the SHG device 67, 68 each produces light 65, 66 of frequency $\omega_3$ ($=2\omega_2$), which is the second harmonic wave of the light 51 of the smaller frequency $\omega_2$. Since the light 65, 66 has the same direction of polarization (the extraordinary direction of the KTiOPO$_4$ crystal) as that of the light 53 of the larger frequency, having passed without change through the SHG device 67, 68, they interfere with each other. Interference light 69, 70 is received by the photodetector 71, 72, respectively. Since the other operation is the same as in the second embodiment, the description thereof is omitted herein.

Now, the configuration of the direction-of-polarization rotating apparatus 401, 402, 411, 412 is explained. Brief description thereof is first provided prior to description of embodiments of the rotating apparatus.

Figure 24:
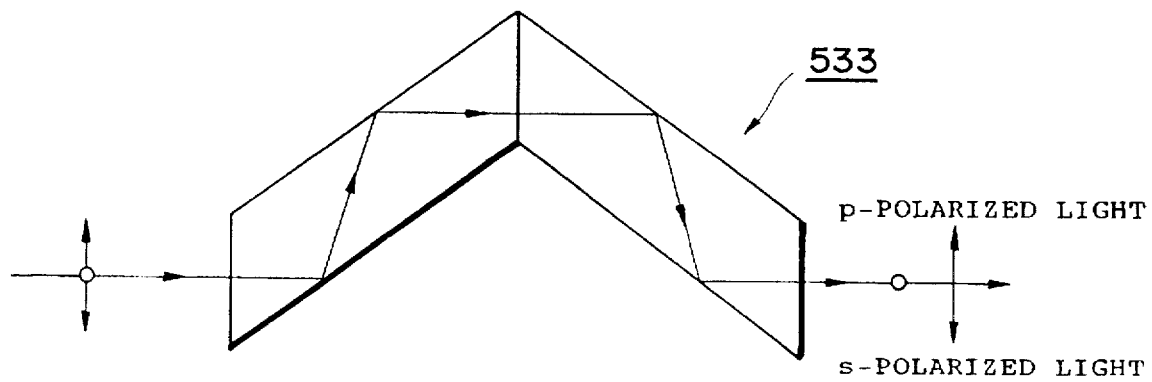
FIG. 24 is an explanatory drawing to show an optical path of a Fresnel rhomb half wave plate.
Figure 25:
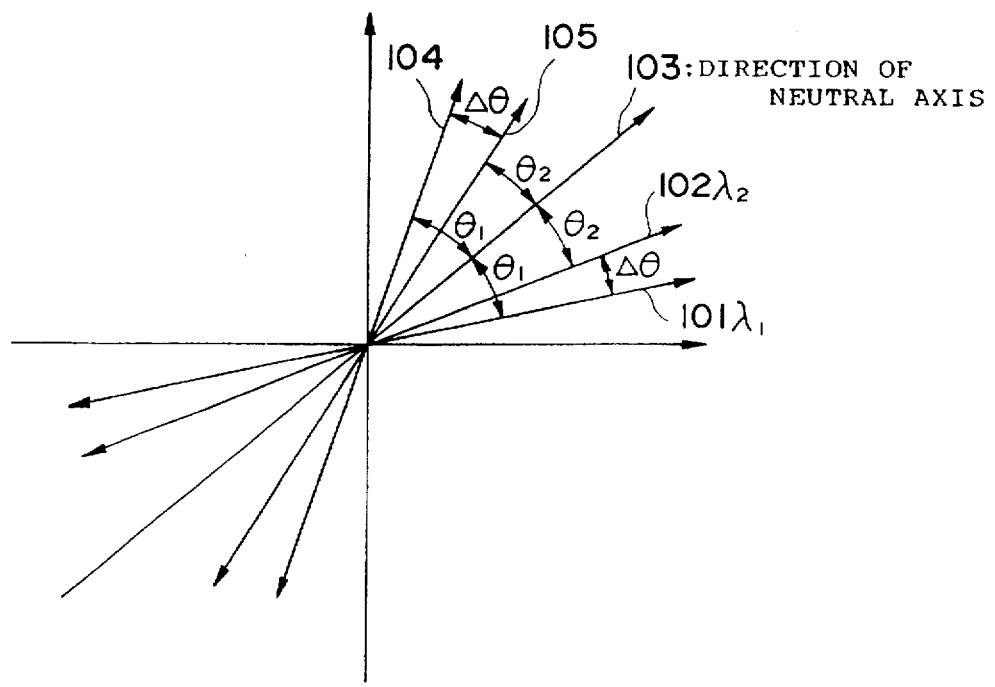
FIG. 25 is an explanatory drawing to show directions of polarization of light before and after passage of the Fresnel rhomb half wave plate.

As means for rotating directions of polarization of coaxial beams consisting of two light beams of different wavelengths there has been used a wave plate having a retardation (a phase difference between natural directions of polarization orthogonal to each other) of $\pi$ for the light beams of the respective wavelengths. For example, a Fresnel rhomb half wave plate is one example thereof. The Fresnel rhomb half wave plate is a plate utilizing phase jump of p-polarized light and s-polarized light in total reflection as shown in FIG. 24. Since the phase jump has little wavelength dependence, phase jump of $\pi$ can be given to each of the light beams of the two frequencies. As shown in FIG. 25, directions of polarization 101, 102 of light beams of two frequencies incident into the Fresnel rhomb half wave plate are rotated to directions 104, 105 symmetric therewith with respect to a neutral axis 103 of the wave plate, after travel therethrough.

However, because the Fresnel rhomb half wave plate rotates the light beams of the two wavelengths each to the directions symmetric with respect to the neutral axis 103, an angle $\Delta\theta$ between the directions of polarization of the light beams of the two wavelengths shows no change between before being incident upon the Fresnel rhomb and after emerging from the Fresnel rhomb. Thus, the Fresnel rhomb half wave plate has a drawback that the directions of polarization of the light beams of the two wavelengths cannot be rotated independently of each other to respective arbitrary directions.

It is, therefore, an object of the present invention to provide a direction-of-polarization rotating apparatus which can rotate the directions of polarization of light beams of two wavelengths independently of each other.

A first aspect of the present invention, for achieving the above object, provides a direction-of-polarization rotating apparatus comprising in order on the optical path, a first wave plate having a retardation $(2n-1)\pi$ for first light beam and second light, and a second wave plate having a retardation $(2m-1)\pi$ for the first light and a retardation $2p\pi$ for the second light. Here, n, m, p are integers.

A second aspect of the present invention, for achieving the above object, comprises in order on the optical path, a first wave plate having a retardation $(2n-1)\pi/2$ for first light and a retardation $(2m-1)\pi$ for second light, a second wave plate having a retardation $(2p-1)\pi/2$ for the first light and a retardation $(2q-1)\pi$ for the second light, and a third wave plate having a retardation $(2r-1)\pi$ for the first light and a retardation $2s\pi$ for the second light. Here, n, m, p, q, r, s are integers.

The present invention permits the directions of polarization of coaxial light beams of two wavelengths to be rotated to respective aimed directions independently of each other.

A retardation $\delta$ of a wave plate utilizing double refraction is given by the following equation when $\lambda$ is a wavelength of light, $n_0$ is a refractive index for ordinary ray, $n_e$ is a refractive index for extraordinary ray, and d is the thickness of the wave plate.

$$\begin{aligned}\delta &= (2\pi/\lambda) \cdot \{n_e(\lambda) - n_o(\lambda)\} \cdot d \\ &= (2\pi\omega) \cdot \{n_e(\omega) - n_o(\omega)\} \cdot d\end{aligned} \quad \text{(Eq. 12)}$$

In Eq. 12, a wavelength dependence of $(n_e-n_o)$ is small. For example, in the case of quartz crystal, a change amount of $(n_e-n_0)$ is 0.0008 in the wavelength range $\lambda$=400 nm to 1000 nm. Accordingly, a certain wave plate has a retardation $\delta=(2n-1)\pi/2$ for first light as functioning as a quarter wave plate, while the wave plate has a retardation $\delta \approx (2m-1)\pi$ for second light having a wavelength equal to the half of a wavelength of the first light as functioning as a half wave plate. Here, n, m are integers.

Further, a certain wave plate has a retardation $\delta=(2q-1)\pi$ for the first light as functioning as a half wave plate, while it has a retardation $\delta \approx 2s\pi$ for the second light as functioning as a one wave plate. Here, q, s are integers.

It is also possible in Eq. 12 to determine such d as to be $\delta=(2t-1)\pi/2$ for the first light and $\delta=(2u-1)\pi/2$ for the second light, utilizing a small difference of $(n_e-n_0)$. Here, t, u are integers where t≠u. The wave plate having this thickness d functions as a quarter wave plate for the first and second light.

It is also possible in Eq. 12 to determine such d as to be $\delta=(2v-1)\pi$ for the first light and $\delta=(2w-1)\pi$ for the second light, utilizing a small difference of $(n_e-n_0)$. The wave plate having this thickness d functions as a half wave plate for the first and second light. Here, v, w are integers where v≠w.

Further, because the wave plate utilizing the phase jump in reflection at a boundary surface, between the p-polarized light and the s-polarized light, has only a small wavelength dependence of the phase jump, it gives nearly equal retardations to the first and second light. Then, in a manner similar to a Fresnel rhomb prism, when it functions as a half wave plate for the first light, it also functions as a half wave plate for the second light. When it functions as a quarter wave plate for the first light, it also functions as a quarter wave plate for the second light.

When these wave plates are thus used to construct the direction-of-polarization rotating apparatus in the first and second aspects of the present invention, directions of polarization of incident light including the first and second light can be rotated as described below.

First, in the case of the direction-of-polarization rotating apparatus in the first aspect of the present invention, the neutral axis of the first wave plate is set along a direction whereby the direction of polarization of the second light included in the incident light is rotated to an aimed direction of polarization. Further, the neutral axis of the second wave plate is set along a direction whereby the direction of polarization of the first light included in the light emerging from the first wave plate is rotated to an aimed direction of polarization. Then the light is let to be incident upon the first wave plate and the second wave plate in the named order. Since the first wave plate functions as a half wave plate for the first and second light, the direction of polarization of the second light is rotated to the aimed direction of polarization. The direction of polarization of the first light is also rotated. Since the second wave plate functions as a half wave plate for the first light and a one wave plate for the second light, the direction of polarization of the first light included in the light emerging from the first wave plate is rotated to the aimed direction of polarization. The direction of polarization of the second light is maintained in the aimed direction of polarization. Thus, the directions of polarization of the first and second light are rotated to the respective aimed directions of polarization.

In the case of the direction-of-polarization rotating apparatus in the second aspect, the neutral axis of the first wave plate is set along a direction whereby the direction of polarization of the first light is changed into circularly polarized light. The neutral axis of the second wave plate is set along a direction whereby the direction of polarization of the second light included in the light emerging from the first wave plate is rotated to an aimed direction of polarization. The neutral axis of the third wave plate is set along a direction whereby the direction of polarization of the first light included in the light emerging from the second wave plate is rotated to an aimed direction of polarization.

Then the first and second light is let to be incident upon the first, second, and third wave plates in the named order. Since the first wave plate functions as a quarter wave plate for the first light and as a half wave plate for the second wavelength light, the first light becomes circularly polarized light and the second light remains as linearly polarized light with the direction of polarization rotated. Since the second wave plate functions as a quarter wave plate for the first light and a half wave plate for the second light, the first light included in the light emerging from the first wave plate changes from the circularly polarized light into linearly polarized light, and the direction of polarization of the second light included in the light emerging from first wave plate is rotated to the aimed direction of polarization. Since the third wave plate functions as a half wave plate for the first light and a one wave plate for the second light, the direction of polarization of the second light included in the light emerging from the second wave plate is maintained in the aimed direction of polarization, and the direction of polarization of the first light is rotated to the aimed direction of polarization. Accordingly, the directions of polarization of the first and second light can be rotated to the respective aimed directions of polarization.

Next, the direction-of-polarization rotating apparatus is explained in further detail.

Figure 19A:
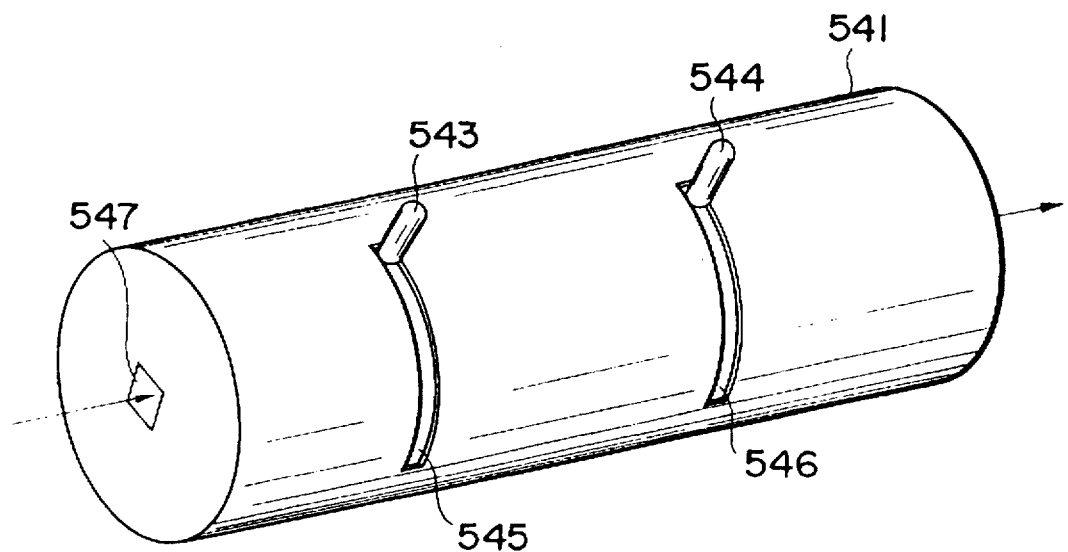
FIGS. 19A and 19B are a perspective view and a partly broken perspective view, respectively, to show the configuration of the entire direction-of-polarization rotating apparatus of FIG. 15.
Figure 19B:
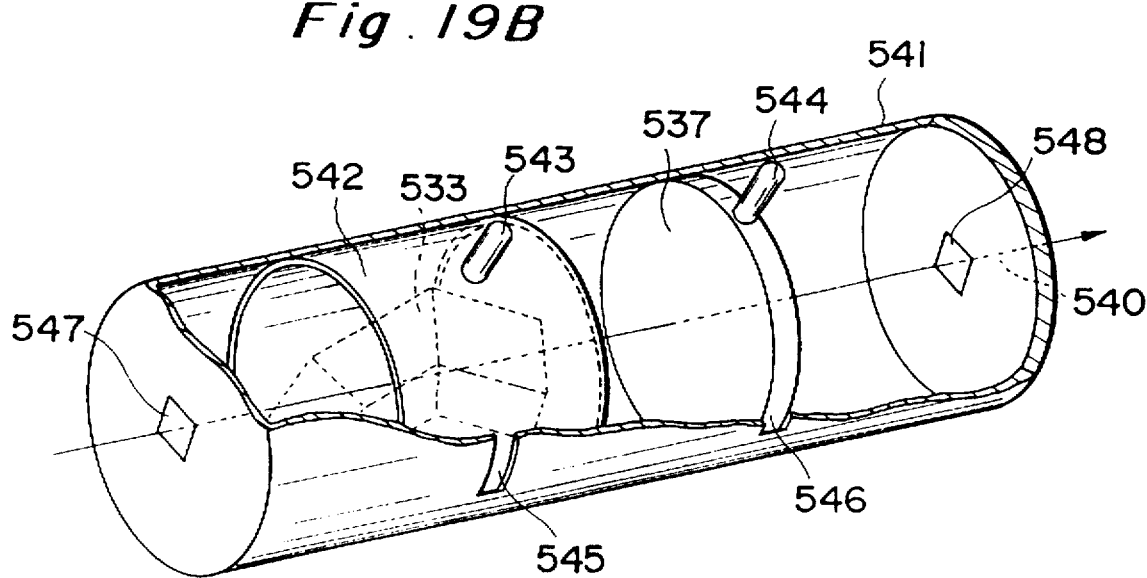

The direction-of-polarization rotating apparatus 401, 402, 412 is constructed, as shown in FIGS. 19A and 19B, of a Fresnel rhomb half wave plate (hereinafter referred to as a Fresnel rhomb) 533 and a wave plate 537 utilizing double refraction of quartz crystal arranged in the named order from the entrance side of light on the optical path 540. The Fresnel rhomb 533 is fixed in a cylinder 542. A handle 543 is attached to the outer surface of the cylinder 542. The wave plate 537 is a disk, to the side surface of which a handle 544 is attached.

The cylinder 542 and wave plate 537 are arranged in a cylindrical casing 541 inside which there is a space. The handles 543, 544 project outward through slits 545, 546 provided along the circumferential direction in the side surface of the casing 541. The casing 541 is provided with windows 547, 548 for letting incident light and emergent light pass. When the handle 543, 544 is moved along the slit 545, 546, the side face of the cylinder 542 or the side face of the wave plate 537 slides on the inner side surface of the casing 541 to rotate the Fresnel rhomb 533 or the wave plate 537, respectively. This permits the neutral axis 532 of the Fresnel rhomb 533 or the neutral axis 536 of the wave plate 537 to be oriented at an arbitrary angle.

The Fresnel rhomb 533 is an element utilizing the fact that a difference becomes $\frac{1}{4}\pi$ between phase jump of the p-polarized light and phase jump of the s-polarized light in a total reflection on a boundary surface, as shown in FIG. 24, which can give a difference of phase jump of $\pi$ by four total reflections. Since the difference of phase jump shows short wavelength dependence, it can give the difference of phase jump of $\pi$ for each of light beams of two wavelengths.

The wave plate 537 is an element utilizing double refraction of quartz crystal. In the wave plate utilizing double refraction, the wavelength dependence is small for the difference $(n_e-n_o)$ between the refractive index $n_o$ for ordinary ray and the refractive index $n_e$ for extraordinary ray. Accordingly, in Eq. 12, $\{n_e(\lambda_1)-n_o(\lambda_1)\}\cdot d$ and $\{n_e(\lambda_2)-n_o(\lambda_2)\}\cdot d$ as to the two wavelengths $\lambda_1$, $\lambda_2$ (where $\lambda_2=(\frac{1}{2})\lambda_1$, frequencies $\omega_4$, $\omega_5$) are nearly equal to each other. Since the present embodiment is arranged in such a manner that the thickness d of the wave plate 537 becomes $\delta=(2n-1)\pi$ (where n is an integer) for the light of wavelength $\lambda_1$, it becomes $\delta=2m\pi$ (where m is an integer) for the light of wavelength $\lambda_2$ ($=(\frac{1}{2})\lambda_1$). Hence, the wave plate 537 serves as a half wave plate for the light of wavelength $\lambda_1$ but as a one wave plate for the light of wavelength $\lambda_2$.

In order to use the direction-of-polarization rotating apparatus of FIGS. 19A and 19B as the direction-of-polarization rotating apparatus 401, 402 of the third embodiment, the thickness of the wave plate is determined by setting $\omega_4=\omega_2$ and $\omega_5=\omega_3$. In order to use the direction-of-polarization rotating apparatus of FIGS. 19A and 19B as the direction-of-polarization rotating apparatus 411, 412 of the fourth embodiment, the thickness of the wave plate is determined by setting $\omega_4=\omega_2$ and $\omega_5=\omega_3'$.

Next explained is the operation for rotating directions of polarization of the two light beams of wavelengths $\lambda_1$, $\lambda_2$ to respective arbitrary directions, using the direction-of-polarization rotating apparatus of the first embodiment.

Figure 15:
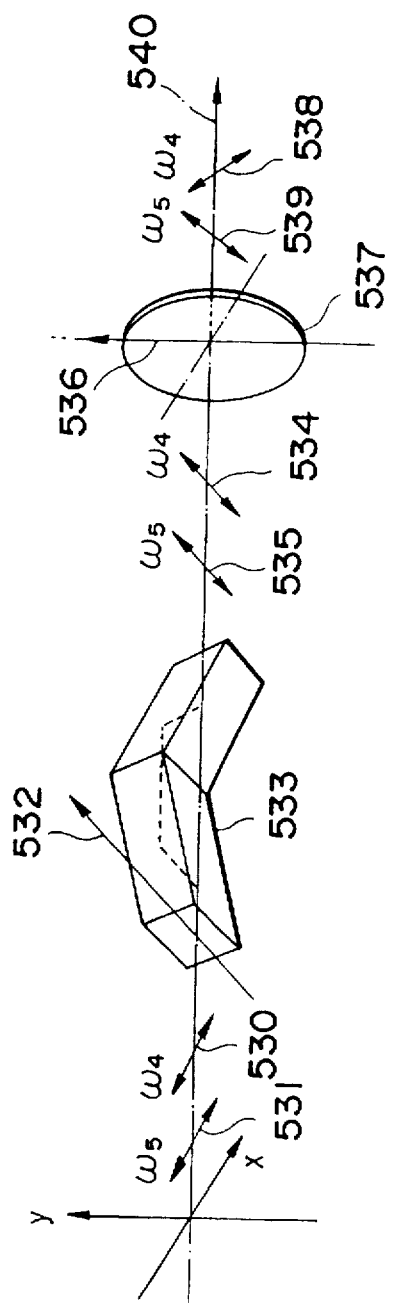
FIG. 15 is an explanatory drawing to show a configuration of a direction-of-polarization rotating apparatus mounted in the light wave interference measuring apparatus in the third or fourth embodiment of the present invention.
Figure 16B:
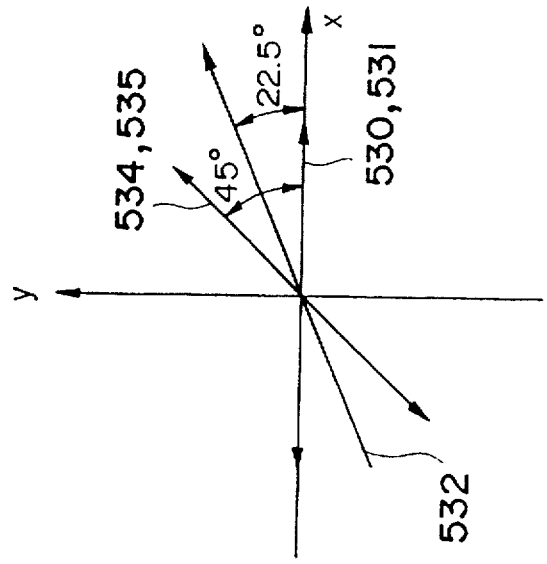
FIGS. 16A and 16B are explanatory drawings to show directions of polarization in the direction-of-polarization rotating apparatus of FIG. 15.
Figure 16A:
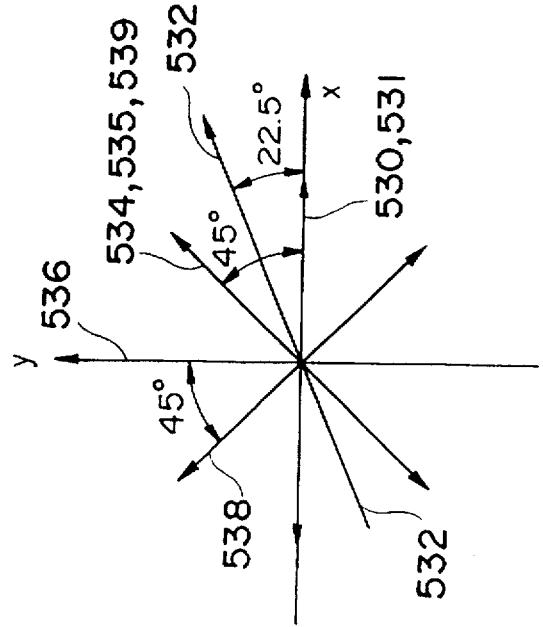

Let us explain referring to FIG. 15 and FIGS. 16A and 16B an example in which light 530 of $\lambda_1$ and light 531 of $\lambda_2$ having the direction of polarization parallel to the x-axis are let to be incident upon the direction-of-polarization rotating apparatus, whereby the light 530 is rotated to change the direction of polarization from the x-axis to +135° to be emergent as light 538 and the light 531 is rotated to change the direction of polarization from the x-axis to +45° to be emergent as light 539. It is noted here that the directions of polarization that can be rotated by the direction-of-polarization rotating apparatus of the present embodiment are not limited to these directions, but incident light of wavelengths $\lambda_1$, $\lambda_2$ having any directions of polarization can be rotated independently of each other to yield emergent light having arbitrary directions of polarization.

First, the handle 543 of the direction-of-polarization rotating apparatus is moved along the slit 545 to rotate the Fresnel rhomb 533 so that the direction of polarization of the light 531 of wavelength $\lambda_2$ may be aligned with an aimed direction. Specifically, in this example where the direction of polarization of the light 531 of wavelength $\lambda_2$ is rotated to the direction of +45°, the neutral axis 532 of the Fresnel rhomb 533 is set from the x-axis to an angle of 22.5°.

Next, the wave plate 537 is set so that the direction of polarization of the light 534 of wavelength $\lambda_1$ (frequency $\omega_4$), having passed the Fresnel rhomb 533 set as described above, may be rotated to the aimed direction of polarization. This setting is effected by moving the handle 544 of the direction-of-polarization rotating apparatus along the slit 546. Specifically, the direction of polarization of the light 534 of wavelength $\lambda_1$ having passed the Fresnel rhomb 533 is rotated to be the direction of +45°, and, in order to rotate it to the aimed direction of polarization of +135°, the neutral axis 536 of the wave plate 537 is set along the y-axis direction.

The beams of coaxial light 530 and light 531 of the two wavelengths have the directions of polarization parallel to the x-axis, as described above. When the light 530 and 531 is incident through the window 547 into the direction-of-polarization rotating apparatus of the present embodiment, the light first is incident upon the Fresnel rhomb 533 with the neutral axis 532 making 22.5° relative to the x-axis and the light 530, 531 of $\lambda_1$, $\lambda_2$ turns to linearly polarized light 534, 535 having the directions of polarization of 45° relative to the x-axis, as shown in FIG. 16B. Next, the light 534, 535 of the two wavelengths emerging from the Fresnel rhomb 533 is incident into the wave plate 537 with the neutral axis 536 parallel to the y-axis. Since the wave plate 537 is a wave plate utilizing double refraction, it functions as a half wave plate for the light of wavelength $\lambda_1$ but functions as a one wave plate for the light of wavelength $\lambda_2$ (=(½)$\lambda_1$). When passing the wave plate 537, the direction of polarization (45°) of the light of wavelength $\lambda_2$ is maintained while the direction of polarization of the light of wavelength $\lambda_1$ (frequency $\omega_4$) is rotated by 90° to become 135° (FIG. 16A). Thus, the direction of polarization of the light of $\lambda_1$ becomes perpendicular to the direction of polarization of the light of $\lambda_2$. This permits us to obtain the light 539 of wavelength $\lambda_2$ having the aimed direction of polarization of 45° and the light 538 of the wavelength $\lambda_1$ having the aimed direction of polarization of 135°.

Therefore, when the direction-of-polarization rotating apparatus of FIGS. 19A and 19B is used as the direction-of-polarization rotating apparatus 401, 402 of the third embodiment, the neutral axis 532 of the Fresnel rhomb 533 is set so that the direction of polarization of the light 24 of frequency $\omega_3$ included in the measuring light 27 and the reference light 26 may be rotated to the extraordinary direction of the KTiOPO$_4$ crystal for the SHG devices 35, 34. Further, the neutral axis 536 of the wave plate 537 is set so that the direction of polarization of the light 21 of frequency $\omega_2$ included in the measuring light 27 and the reference light 26 having passed the Fresnel rhomb 533 may be rotated to the direction of polarization near 45° relative to the extraordinary direction of the KTiOPO$_4$ crystal for the SHG devices 35, 34.

Further, when the direction-of-polarization rotating apparatus of FIGS. 19A and 19B is used as the direction-of-polarization rotating apparatus 411, 412 of the fourth embodiment, the neutral axis 532 of the Fresnel rhomb 533 is set so that the direction of polarization of the light 53 of frequency $\omega_3'$ included in the measuring light 60 and the reference light 59 may be rotated to the extraordinary direction of the KTiOPO$_4$ crystal for the SHG devices 68, 67. Further, the neutral axis 536 of the wave plate 537 is set so that the direction of polarization of the light 51 of frequency $\omega_2$ included in the measuring light 60 and the reference light 59 having passed the Fresnel rhomb 533 may be rotated to the direction of polarization near 45° relative to the extraordinary direction of the KTiOPO$_4$ crystal for the SHG devices 68, 67.

In the direction-of-polarization rotating apparatus of FIGS. 19A and 19B as described above, the Fresnel rhomb 533 may be replaced by a wave plate utilizing double refraction to give a retardation (2n−1)π for the light of wavelength $\lambda_1$ (frequency $\omega_4$) and a retardation (2m−1)π for the light of wavelength $\lambda_2$ (frequency $\omega_5$). Here, n, m are natural numbers. Such a wave plate is one having such a thickness d as to be $\delta$=(2n−1)π for the light of frequency $\omega_4$ and to be $\delta$=(2m−1)π for the light of frequency $\omega_5$ in Eq. 12 as discussed above, utilizing a small difference of ($n_e$−$n_o$) in double refraction. The wave plate having such a thickness d functions as a half wave plate for the light of frequency $\omega_4$ and frequency $\omega_5$. Therefore, such a wave plate may replace the Fresnel rhomb 533 in the embodiment of FIGS. 19A and 19B.

The wave plate 37 may be arranged to have retardations the signs of which may be either positive or negative.

Next explained referring to FIG. 17, FIGS. 18A and 18B, and FIGS. 20A and 20B is another direction-of-polarization rotating apparatus which can be used as the direction-of-polarization rotating apparatus 401, 402, 411, 412.

Figure 20A:
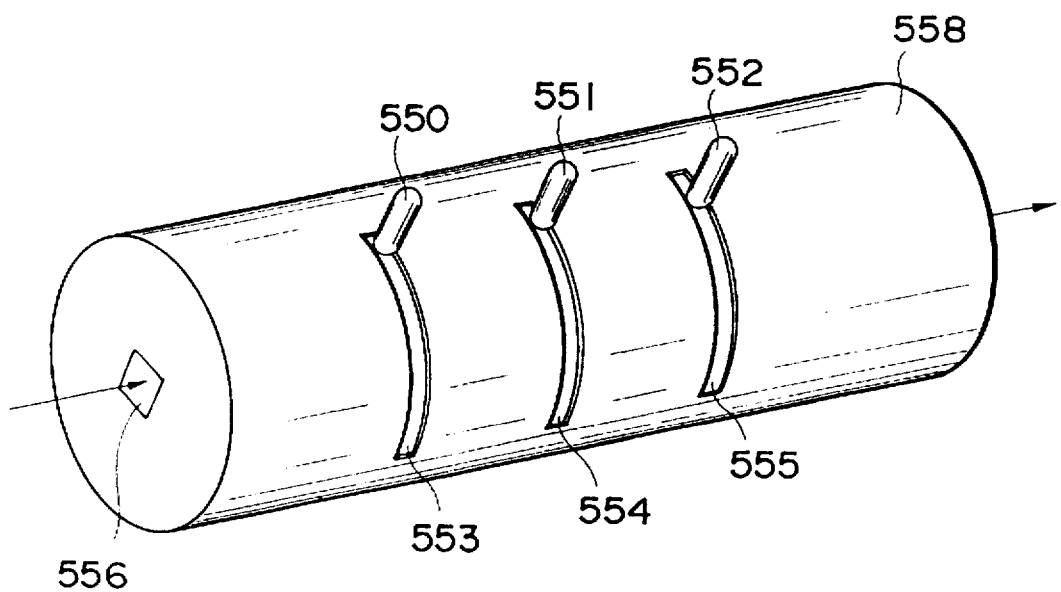
FIGS. 20A and 20B are a perspective view and a partly broken perspective view, respectively, to show the configuration of the entire direction-of-polarization rotating apparatus of FIG. 17.
Figure 20B:
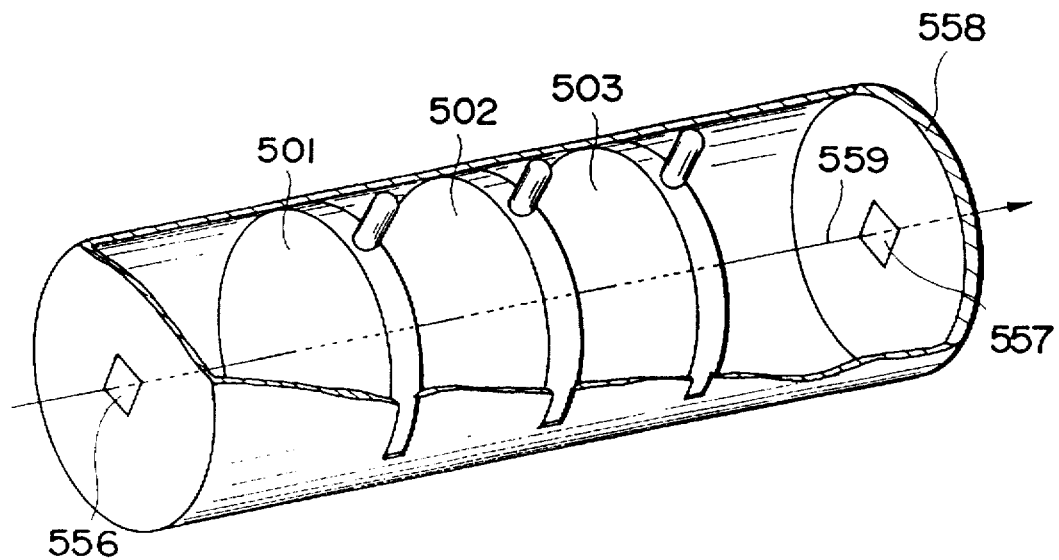

This direction-of-polarization rotating apparatus is constructed, as shown in FIGS. 20A and 20B, of a wave plate 501, a wave plate 502, and a wave plate 503 arranged in the named order from the entrance side of light on the optical path 559. A handle 550 is attached to the wave plate 501, a handle 551 to the wave plate 502, and a handle 552 to the wave plate 503.

The wave plate 501, wave plate 502, and wave plate 503 are arranged inside a cylindrical casing 558 inside which there is a space. The handles 550, 551, 552 project outward through corresponding slits 553, 554, 555 provided along the circumferential direction in the side surface of the casing 558. The casing 558 is provided with windows 556, 557 for letting incident light and emergent light pass. When the handle 550, 551, 552 is moved along the slit 553, 554, 555, the neutral axis 504, 505, 506 of the wave plate 501, 502, 503 can be oriented each at an arbitrary angle.

The wave plate 501, wave plate 502, and wave plate 503 are those utilizing double refraction of quartz crystal. As already described, the wave plates utilizing double refraction show such properties that the difference of ($n_0$−$n_e$) between the refractive index $n_0$ for ordinary ray and the refractive index $n_e$ for extraordinary ray has only a small wavelength dependence and that in Eq. 12 as discussed above, $\{n_e(\omega_4)-n_0(\omega_4)\}\cdot d$ and $\{n_e(\omega_5)-n_0(\omega_5)\}\cdot d$ as to the two wavelengths $\omega_4$, $\omega_5$ (where $\omega_5$=2$\omega_4$) are nearly equal to each other. In the direction-of-polarization rotating apparatus of FIGS. 20A and 20B, the thicknesses d of the wave plate 501, wave plate 502, and wave plate 503 are determined so as to be $\delta$=π/2 (i.e., a quarter wave plate), $\delta$=π/2 (i.e., a quarter wave plate), and $\delta$=π (i.e., a half wave plate), respectively, for the light of frequency $\omega_4$. For the light of frequency $\omega_5$ (=2$\omega_4$), they become $\delta$=π (i.e., a half wave plate), $\delta$=π (i.e., a half wave plate), and $\delta$=2π (i.e., a one wave plate), respectively.

In other words, in Eq. 12, $\{n_e(\lambda_1)-n_0(\lambda_1)\}\cdot d$ and $\{n_e(\lambda_2)-n_0(\lambda_2)\}\cdot d$ as to the two wavelengths $\lambda_1$, $\lambda_2$ (where $\lambda_2$=½$\lambda_1$) are nearly equal to each other. Since the present embodiment is arranged so that the thicknesses d of the wave plate 501, wave plate 502, and wave plate 503 may be $\delta$ (2n−1)π/2 (i.e., a quarter wave plate), $\delta$=(2p−1)π/2 (i.e., a quarter wave plate), and $\delta$=2(r−1)π (i.e., a half wave plate), respectively, for the light of wavelength $\lambda_1$, they become $\delta$=(2m−1)π (i.e., a half wave plate), $\delta$=(2q−1)π (i.e., a half wave plate), and $\delta$=2sπ (i.e., a one wave plate), respectively, for the light of wavelength $\lambda_2$ (=½$\lambda_1$). Here, n, m, p, q, r, s are integers.

However, when the direction-of-polarization rotating apparatus of FIGS. 20A and 20B is used as the direction-of-polarization rotating apparatus 401, 402 of the third embodiment, the thicknesses of the wave plates are determined as setting $\omega_4=\omega_2$ and $\omega_5=\omega_3$. Further, when the direction-of-polarization rotating apparatus of FIGS. 20A and 20B is used as the direction-of-polarization rotating apparatus 411, 412 of the fourth embodiment, the thicknesses of the wave plates are determined as setting $\omega_4=\omega_2$ and $\omega_5=\omega_3'$.

Next explained is the operation for rotating the directions of polarization of the two light beams of frequencies $\omega_4$, $\omega_5$ to respective arbitrary directions, using the direction-of-polarization rotating apparatus of FIGS. 20A and 20B.

Figure 17:
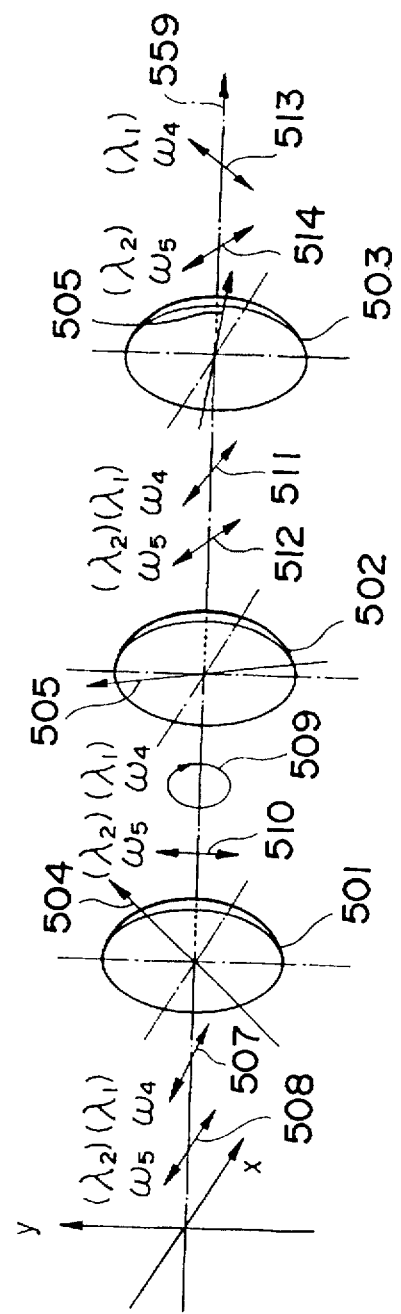
FIG. 17 is an explanatory drawing to show another configuration of the direction-of-polarization rotating apparatus mounted in the light wave interference measuring apparatus in the third or fourth embodiment of the present invention.
Figure 18A:
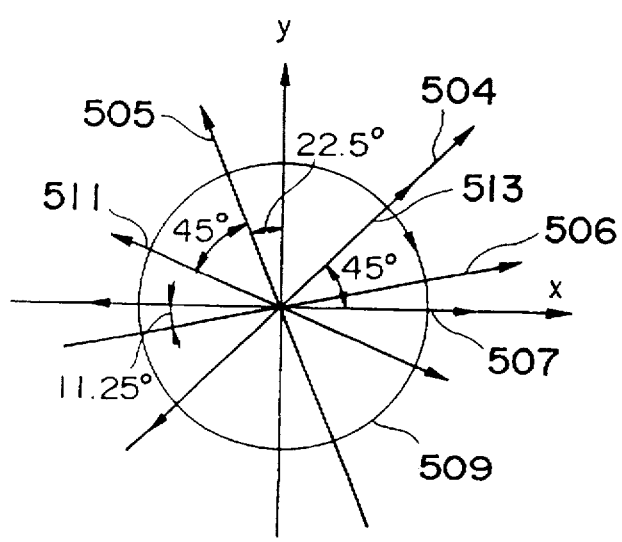
FIGS. 18A and 18B are explanatory drawings to show directions of polarization in the direction-of-polarization rotating apparatus of FIG. 17.
Figure 18B:
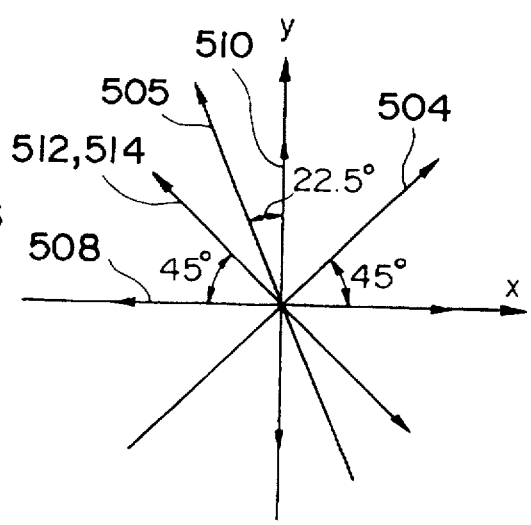

Let us explain an example, as shown in FIG. 17 and FIGS. 18A and 18B, where beams of light 507 of $\omega_4$ and light 508 of $\omega_5$ (=$2\omega_4$) having the direction of polarization parallel to the x-axis are let to be incident upon this direction-of-polarization rotating apparatus so that the light 508 may be rotated from the x-axis into light 514 having a direction of polarization of +135° and so that the light 507 may be rotated from the x-axis into light 513 having a direction of polarization of +45°. It is noted here that the directions of polarization which can be rotated by the direction-of-polarization rotating apparatus of FIGS. 20A and 20B are not limited to these directions, but the incident light of frequencies $\omega_4$, $\omega_5$ having any directions of polarization can be rotated independently of each other to achieve emergent light having arbitrary directions of polarization.

First, the handle 550 of the direction-of-polarization rotating apparatus is moved along the slit 553 to set the wave plate 501 so that the direction of polarization of the light 507 of frequency $\omega_4$ may turn into circular polarization. Specifically, in this example, because the light 507 of frequency $\omega_4$ has the direction of polarization parallel to the x-axis, the neutral axis 504 of the wave plate 501 is set at an angle of 45° from the x-axis.

Next, the wave plate 502 is set so that the direction of polarization of the light 510 of frequency $\omega_5$, having passed the wave plate 501 thus set as described above, may be rotated to an aimed direction of polarization. This setting can be achieved by moving the handle 551 of the direction-of-polarization rotating apparatus along the slit (slot) 554. Specifically, because the wave plate 501 functions as a half wave plate for the light of frequency $\omega_5$, the direction of polarization of the light 510 of frequency $\omega_5$, having passed the wave plate 501, is rotated to the direction of the y-axis, and then it needs to be rotated to the aimed direction of polarization of +135°. Here, because the wave plate 502 functions as a half wave plate for the light of frequency $\omega_5$, as discussed above, the neutral axis 505 of the wave plate 502 is set along the direction of 112.5° relative to the x-axis.

Further, the wave plate 503 is set so that the direction of polarization of the light 511 of wavelength $\omega_4$, having passed the wave plate 502 thus set as discussed above, may be rotated to the aimed direction of polarization. This setting may be achieved by moving the handle 552 of the direction-of-polarization rotating apparatus along the slit (slot) 555. Specifically, because the direction of polarization of the light 511 of frequency $\omega_4$ having passed the wave plate 502 is rotated to the direction of 157.5° from the x-axis, it needs to be rotated to the aimed direction of polarization of 45°. Thus, the neutral axis 506 of the wave plate 503 is set along the direction of 11.25° from the x-axis.

Next explained are the directions of polarization of the light 507, 509, 511, 513 of wavelength $\lambda_1$ (frequency $\omega_4$) with FIG. 18A and the directions of polarization of the light 508, 510, 512, 514 of wavelength $\lambda_2$ (frequency $\omega_5$) with FIG. 18B. The coaxial light 507, 508 of the two wavelengths have the direction of polarization parallel to the x-axis. When the light 507, 508 is incident through the window 556 into the direction-of-polarization rotating apparatus of FIGS. 20A and 20B, the light first be incident upon the wave plate 501 with the neutral axis 504 making 45° relative to the x-axis. Since the wave plate 501 functions as a quarter wave plate for the light of frequency $\omega_4$ and as a half wave plate for the light of frequency $\omega_5$, the light 507 of frequency $\omega_4$ turns into circularly polarized light 509 and the light 508 of frequency $\omega_5$ turns 90° to become linearly polarized light 510 parallel to the y-axis.

Next, the light 509, 510 of the two wavelengths emerging from the wave plate 501 be incident upon the wave plate 502 with the neutral axis 505 making 112.5° relative to the x-axis. Since the wave plate 502 functions as a quarter wave plate for the light of frequency $\omega_4$ but as a half wave plate for the light of frequency $\omega_5$, the linearly polarized light 510 of frequency $\omega_5$ turns into linearly polarized light 512 making an angle of 135° relative to the x-axis, and the circularly polarized light 509 of frequency $\omega_4$ turns into linearly polarized light 511 making an angle of 45° relative to the neutral axis 505 (or making an angle 157.5° relative to the x-axis).

Further, the light 511, 512 of the two wavelengths emerging from the wave plate 502 is incident into the wave plate 503 with the neutral axis 506 making 11.25° relative to the x-axis. Here, since the wave plate 503 functions as a half wave plate for the light of frequency $\omega_4$ but as a one wave plate for the light of frequency $\omega_5$, the direction of polarization of the light 512 of frequency $\omega_5$ is maintained in the aimed direction of polarization while the direction of polarization of the light 511 of frequency $\omega_4$ turns to the direction of 45° relative to the x-axis. As described above, the light of the two wavelengths ($\omega_4=2\omega_5$) 507, 508 having the directions of polarization parallel to each other turns into the light 513, 514 of the two wavelengths having the aimed directions of polarization inclined 45° and perpendicular to each other.

Thus, when the direction-of-polarization rotating apparatus of FIGS. 20A and 20B is used as the direction-of-polarization rotating apparatus 401, 402 of the third embodiment, the neutral axis 504 of the wave plate 501 is set so that the direction of polarization of the light 21 of frequency $\omega_2$ included in the measuring light 27 and the reference light 26 may turn into circular polarization. Further, the neutral axis 505 of the wave plate 502 is set so that the direction of polarization of the light 24 of frequency $\omega_3$ included in the measuring light 27 and the reference light 26, having passed the wave plate 501 thus set as described above, may be rotated to the extraordinary direction of the KTiOPO$_4$ crystal for the SHG devices 35, 34. Further, the neutral axis 506 of the wave plate 503 is set so that the direction of polarization of the light 21 of frequency $\omega_2$ included in the measuring light 27 and the reference light 26 having passed the wave plate 502 may be rotated to the direction of polarization near 45° relative to the extraordinary direction of the KTiOPO$_4$ crystal for the SHG devices 35, 34.

Further, when the direction-of-polarization rotating apparatus of FIGS. 20A and 20B is used as the direction-of-polarization rotating apparatus 411, 412 of the fourth embodiment, the neutral axis 504 of the wave plate 501 is set so that the direction of polarization of the light 51 of frequency $\omega_2$ included in the measuring light 60 and the reference light 59 may turn into circular polarization. Further, the neutral axis 505 of the wave plate 502 is set so that the direction of polarization of the light 53 of frequency $\omega_3'$ included in the measuring light 60 and the reference light 59, having passed the wave plate 501 thus set as described above, may be rotated to the extraordinary direction of the KTiOPO$_4$ crystal for the SHG devices 68, 67. Further, the neutral axis 506 of the wave plate 503 is set so that the direction of polarization of the light 51 of frequency $\omega_2$ included in the measuring light 60 and the reference light 59 having passed the wave plate 502 may be rotated to the direction of polarization near 45° relative to the extraordinary direction of the KTiOPO$_4$ crystal for the SHG devices 68, 67.

Since in the third or fourth embodiment the direction-of-polarization rotating apparatus of FIGS. 19A and 19B or FIGS. 20A and 20B as described above is located before the SHG devices 34, 35, 67, 68, the light of frequency $\omega_2$ can be made incident in the direction of polarization in which a conversion efficiency of SHG device into the second harmonic wave is high. Further, the SHG device can transmit the light of frequency $\omega_3$ or $\omega_3'$ so that the light of frequency $\omega_3$ or $\omega_3'$ can be made incident in the direction of polarization in which the second harmonic wave of frequency $\omega_2$ is emergent. Thus, the second harmonic wave can be obtained with high intensity. Since the light of frequency $\omega_3$ as the second harmonic wave is coincident in the direction of polarization with the light of frequency $\omega_3$ or $\omega_3'$ as transmitted light, interference light can be obtained with high intensity. The true displacement D and refractive index can be monitored with accuracy accordingly.

The direction-of-polarization rotating apparatus of FIGS. 19A, 19B or FIGS. 20A, 20B has the casing 541 or 558, but it is also possible to arrange only the wave plates in line at the position of the direction-of-polarization rotating apparatus 401, 402, 411, 412 in the light wave interference measuring apparatus of FIG. 13 or FIG. 14. In this case, the neutral axes of the wave plates may be stationarily set in accordance with the crystal orientation of the SHG device.

The above embodiment shown in FIG. 17 is arranged so that the signs of the retardation values of the wave plates 501, 502, 503 are positive, negative, and positive in order, but the present embodiment is not limited to this combination of signs. The signs of the retardation values may be arbitrarily determined positive or negative as long as absolute values of the retardations of the three wave plates 501, 502, 503 are equal to those of the wave plates 501, 502, 503 in the embodiment of FIG. 17. In the cases where the combination of the signs of retardations of the three wave plates is different from that in the embodiment of FIG. 17, a way of setting the neutral axis of each wave plate is determined based on the directions of polarization upon incidence of the light of wavelengths $\lambda_1$, $\lambda_2$ and aimed directions of polarization, in the same manner as in the embodiment of FIG. 17.

Figure 22:
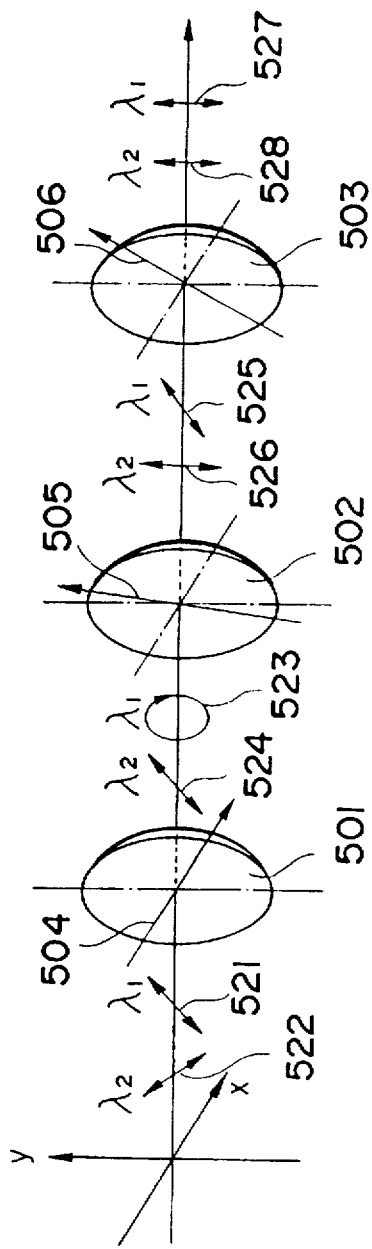
FIG. 22 is an explanatory drawing to show another way of using the direction-of-polarization rotating apparatus of the embodiment shown in FIG. 20.
Figure 23A:
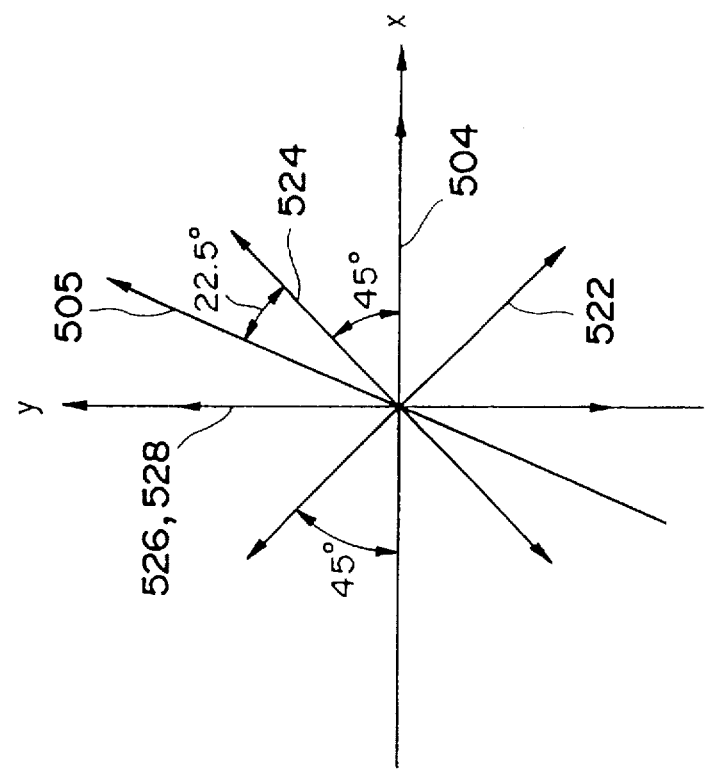
FIGS. 23A and 23B are explanatory drawings to show directions of polarization in the direction-of-polarization rotating apparatus in the case of the using way of FIG. 22.
Figure 23B:
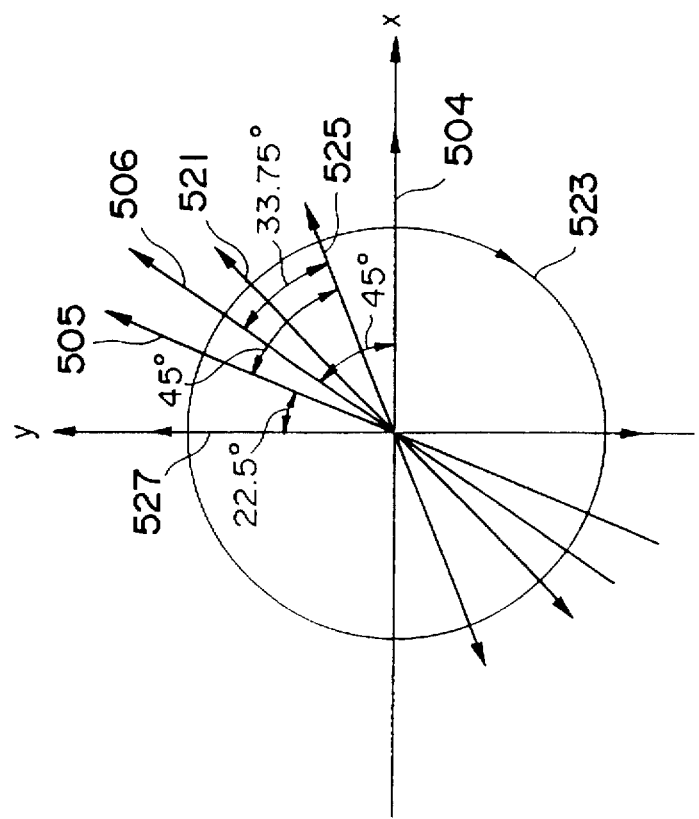

Now explained referring to FIG. 22 and FIGS. 23A and 23B is an example in which the light beams of two wavelengths ($\lambda_1=2\lambda_2$) having directions of polarization perpendicular to each other are rotated +45° and −45°, respectively, to become parallel to each other, using a direction-of-polarization rotating apparatus having retardations absolute values of which are the same as those of the wave plates 501, 502, 503 in the above embodiment of FIG. 17 but the signs of which are positive, positive, and positive.

Coaxial light beams of linearly polarized light 521, 522 of the two wavelengths have directions of polarization making respective angles of 45° and 135° relative to the x-axis and perpendicular to each other. First, the neutral axis 504 of the wave plate 501 is set at an angle of 0° (along the x-axis direction) to change the light 521 of wavelength $\lambda_1$ into circularly polarized light 523. The neutral axis 505 of the wave plate 502 is set at an angle of 67.5° to turn the light 524 of wavelength $\lambda_2$ emerging from the wave plate 501 into light 526 having an aimed direction of polarization. Further, the neutral axis 506 of the wave plate 503 is set at an angle of 56.25° to turn the light 525 of wavelength $\lambda_1$ emerging from the wave plate 502 into light 527 having an aimed direction of polarization.

The light 521 of wavelength $\lambda_1$ and the light 522 of wavelength $\lambda_2$ is incident into the wave plate 501 with the neutral axis 504 being parallel to the x-axis whereby the light 521 of wavelength $\lambda_1$ turns into circularly polarized light 523 (FIG. 23A) and the light 522 of wavelength $\lambda_2$ turns 90° to become linearly polarized light 524 making 45° relative to the x-axis (FIG. 23B). Next, the light 523, 524 of the two wavelengths emerging from the wave plate 501 is incident into the wave plate 502 with the neutral axis 505 making an angle of 67.5°, whereby the light 524 of $\lambda_2$ turns into linearly polarized light 526 parallel to the y-axis and the light 523 of $\lambda_1$ turns into linearly polarized light 525 making an angle of 45° relative to the neutral axis 505 (or making an angle of 22.5° relative to the x-axis). Further, the light 525, 526 of the two wavelengths emerging from the wave plate 502 are incident into the wave plate 503 with the neural axis 506 making an angle of 56.25°, whereby the direction of polarization of the light 525 of wavelength $\lambda_1$ becomes parallel to the y-axis as maintaining the direction of polarization of the light 526 of wavelength $\lambda_2$.

As described above, the light ($\lambda_1=2\lambda_2$) 521, 522 of the two wavelengths having the directions of polarization perpendicular to each other turns into the light 527, 528 of the two wavelengths with the directions of polarization rotated 45° from the original directions and being parallel to each other.

Thus using the first or second direction-of-polarization rotating apparatus, the directions of polarization of the light of the two wavelengths $\lambda_1$, $\lambda_2$ ($\lambda_1=2\lambda_2$) can be rotated independently of each other.

Here, apparatus shown in FIG. 28 to FIG. 31 may be used instead of the polarization rotating apparatus shown in FIG. 17. Two light beams input into each apparatus are beams of linearly polarized light having same directions of polarization and having wavelengths $\lambda_1$ and $\lambda_2$. Here, $\lambda_1=2\lambda_2$.

When these light beams are incident into the wave plate 1501 of FIG. 28, the changes in the directions of polarization of these light beams are the same as in the case of these light beams being input into the Fresnel rhomb prism. This apparatus is provided with two quartz wave plates 1501, 1502 utilizing double refraction, which are located on a same straight line. The wave plate 1501 is a half wave plate ready for two wavelengths, which can rotate the direction of polarization of the light of $\lambda_2$ to an arbitrary direction. The wave plate 1501 also rotates the light of $\lambda_1$ in the same manner as the direction of polarization of the light of $\lambda_2$ is rotated. The wave plate 1502 is a half wave plate for the light of $\lambda_1$, which rotates the direction of polarization of this light to an arbitrary direction. This wave plate 1502 functions as a one wave plate for the light of $\lambda_2$, and thus, the direction of polarization of the light of $\lambda_2$ does not change after passage through this wave plate 1502.

The apparatus of FIG. 29 is arranged by switching the positions of the two wave plates in FIG. 28, which also rotates the direction of polarization of the input light much the same manner as in the apparatus of FIG. 28.

FIG. 30 shows an apparatus obtained by switching the positions of the wave plate 501 and wave plate 503 shown in FIG. 17. The wave plate 503 is located so that when a circularly polarized light of wavelength $\lambda_1$ is let to be incident upon the wave plate 501, the direction of polarization of the light of wavelength $\lambda_1$ rotated by this wave plate 501 can turn into linearly polarized light of aimed polarization. In this case, it is preliminarily calculated which direction the direction of polarization of the light of wavelength $\lambda_2$ should be aligned with before being incident upon the wave plate 501. The wave plate 502 can rotate the direction of polarization of the second light to an arbitrary direction. The wave plate 502 is located so that the direction of polarization of the light of wavelength $\lambda_2$ may have such a direction of polarization change as to be aligned with the direction of polarization calculated from the position of the wave plate 503. The light of wavelength $\lambda_1$ is changed into circularly polarized light by the wave plate 502. Namely, the wave plate 502 functions as a quarter wave plate for the light of wavelength $\lambda_1$. The wave plate 501 rotates the direction of polarization of the light of wavelength $\lambda_1$ to an arbitrary direction. The wave plate 501 is adjusted and located so that the light of wavelength $\lambda_1$ may be changed into circularly polarized light by the wave plate 502. Since the wave plate 501 functions as a one wave plate for the light of wavelength $\lambda_2$, the light of wavelength $\lambda_2$ does not change.

The apparatus of FIG. 31 is provided with wave plates 2501, 2502, 2503, 2504. This apparatus is effective to the cases where two light beams incident into this apparatus deviate from linearly polarized light (or in the cases of elliptically polarized light). The first wave plate 2501 functions as a one-eighth wave plate for the light of wavelength $\lambda_1$. The wave plate 2501 functions as a quarter wave plate for the light of wavelength $\lambda_2$, and, being incident upon this wave plate 2501, the light of wavelength $\lambda_2$ changes from elliptically polarized light into linearly polarized light. Passing through the wave plate 2501, the light of wavelength $\lambda_1$ changes its ellipticity but normally remains as elliptically polarized light. The wave plate 2502 functions as a quarter wave plate for the light of wavelength $\lambda_1$. When the light of wavelength $\lambda_1$ is incident upon this wave plate 2502, the light of wavelength $\lambda_1$ changes from elliptically polarized light into circularly polarized light. This wave plate 2502 functions as a half wave plate for the light of wavelength $\lambda_2$. The wave plates 2503, 2504 are the same as the wave plates 502, 503, respectively, in FIG. 17, which rotate polarization of these input light beams.

Figure 5:
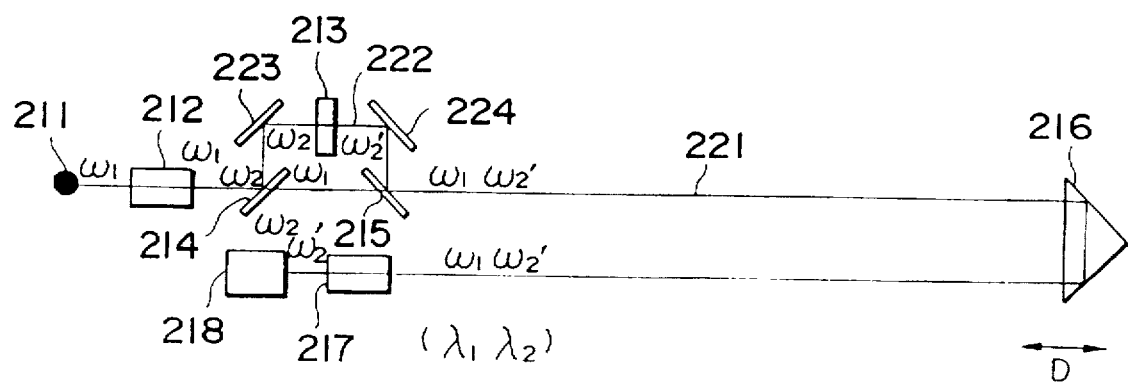
FIG. 5 is a block diagram to show a configuration of the refractive index change measuring apparatus according to a fifth embodiment of the present invention.

Next explained referring to FIG. 5 is a refractive index change measuring apparatus using light wave interference as the fifth embodiment of the present invention.

First explained is the configuration of the apparatus for measuring the change in the refractive index according to the present embodiment. Arranged on an optical path 221 in a space a refractive index change of which is to be measured are a light source 211, an SHG device 212, a dichroic mirror 214, a dichroic mirror 215, a moving mirror 216, an SHG device 217, and a photodetector 218. Further, a mirror 223, a frequency shifter 213, and a mirror 224 are arranged on an optical path 222 of light reflected by the dichroic mirror 214.

The SHG device 212 converts part of light (fundamental wave) of frequency $\omega_1$ emitted from the light source 211 into light of frequency $\omega_2$ ($\omega_2=2\omega_1$: second harmonic wave). The dichroic mirror 214 reflects the light of frequency $\omega_2$. The frequency shifter 213 shifts the frequency $\omega_2$ by a fixed value to get light of frequency $\omega_2'$. The dichroic mirror 215 coaxially multiplexes the light of frequency $\omega_1$ and the light of frequency $\omega_2'$, and the multiplexed light travels in the space the change in the refractive index of which is to be measured and then is reflected by the moving mirror 216 moving in a predetermined displacement. Further, the multiplexed light then travels in the space the index change of which is to be measured. Then the SHG device 217 converts the light of frequency $\omega_1$ into frequency $\omega_2$ ($\omega_2=2\omega_1$). The light of frequency $\omega_2'$ is transmitted by the SHG device 217, so that the light of frequency $\omega_2'$ heterodyne interferometry with the light of frequency $\omega_2$, thus forming interference fringes. The photodetector 218 detects the interference fringes to detect a phase difference.

With this phase difference detected by the photodetector 218, $\{D(\omega_2')-D(\omega_1)\}$, corresponding to a phase difference between two light beams when the displacement of the moving mirror 216 is measured with the two light beams, is obtained in the same manner as in the second embodiment. As explained in the first and second embodiments, $D(\omega_2')-D(\omega_1)$ is the value including information of the change in the refractive index of the air. Accordingly, the refractive index of the air upon measurement can be relatively detected.

Here, if the moving mirror 216 is moved in the constant displacement preliminarily determined, the refractive index upon measurement can be relatively detected by using the phase difference detected by the photodetector 218 as it is. If the moving mirror 216 is displaced by a displacement not being constant, the refractive index upon measurement can be relatively detected by correcting the displacement upon measurement from the phase difference detected by the photodetector 218.

Also, another optical system may be used to measure the displacement of the moving mirror 216 with light of frequency $\omega_3$ and then to obtain $D(\omega_3)$, whereby the true displacement of the moving mirror 216 can be obtained using the following Eq. 13.

$$D=D(\omega_3)-[F(\omega_3)]\{F(\omega_2')-F(\omega_1)\}]\cdot\{D(\omega_2')-D(\omega_1)\} \quad (15)$$

Here, F is a function preliminarily obtained, dependent on the frequency of light.

Further, the refractive index $n(\omega_3)$ upon measurement for the light of frequency $\omega_3$ can be obtained from the true displacement D, using the following equation.

$$n(\omega_3)=D(\omega_3)/D$$

The optical system for measuring the displacement of the moving mirror 216 may be, for example, the optical system for obtaining $D(\omega_1)$ shown in the first and second embodiments. It should be noted that any apparatus that can measure the displacement of the moving mirror 216 can be used without having to be limited to the above optical system.

Figure 6:
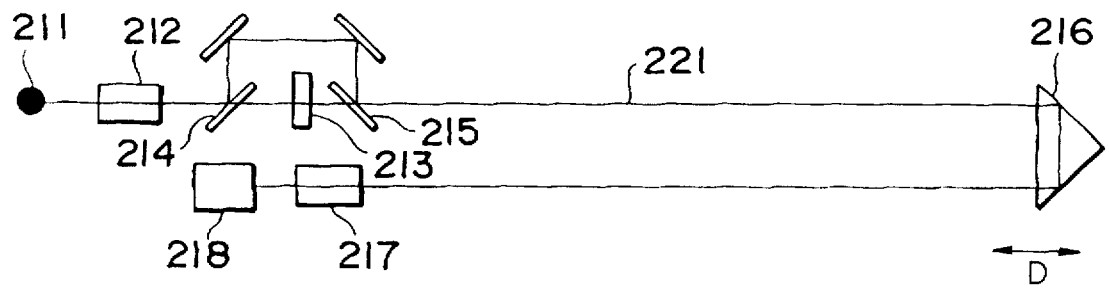
FIG. 6 is a block diagram to show another configuration of the refractive index change measuring apparatus according to the fifth embodiment of the present invention.
Figure 7:
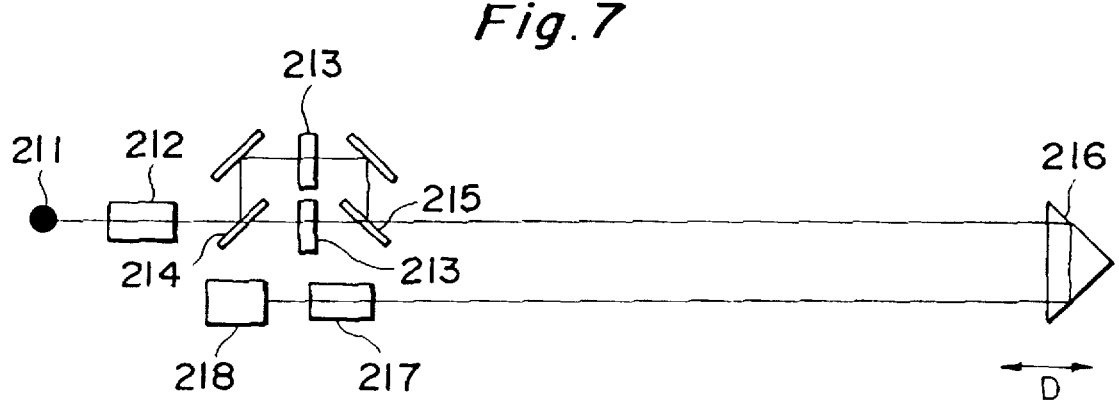
FIG. 7 is a block diagram to show another configuration of the refractive index change measuring apparatus according to the fifth embodiment of the present invention.

Further, the change in the refractive index of the air can also be relatively detected in the same manner by an arrangement in which the frequency shifter 213 is disposed on the optical path 221 to shift the frequency of the fundamental wave, as shown in FIG. 6, or an arrangement in which two frequency shifters 213 are provided to shift the two frequencies of the fundamental wave and the second harmonic wave, as shown in FIG. 7.

Figure 8:
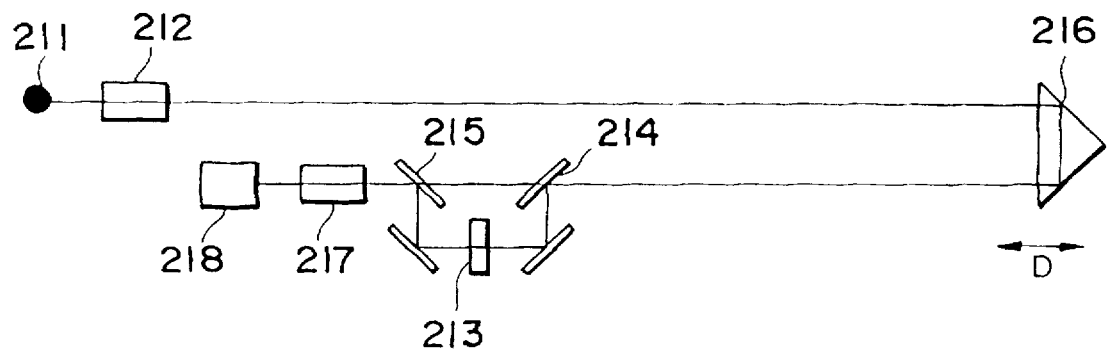
FIG. 8 is a block diagram to show another configuration of the refractive index change measuring apparatus according to the fifth embodiment of the present invention.
Figure 9:
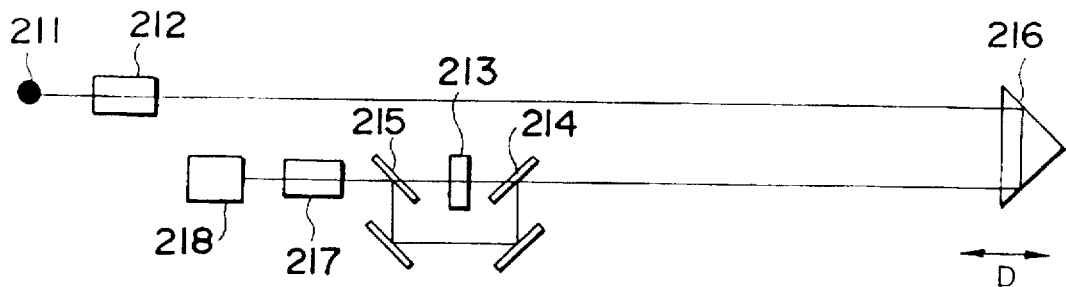
FIG. 9 is a block diagram to show another configuration of the refractive index change measuring apparatus according to the fifth embodiment of the present invention.
Figure 10:
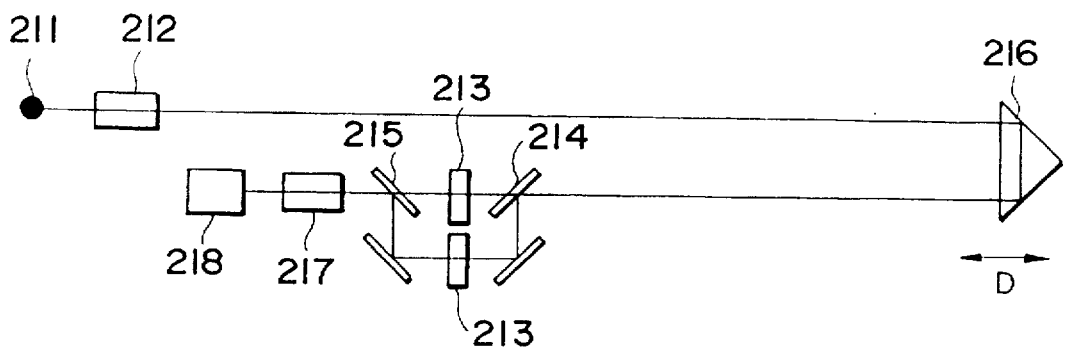
FIG. 10 is a block diagram to show another configuration of the refractive index change measuring apparatus according to the fifth embodiment of the present invention.

Further, the change in the refractive index of the air can also be relatively detected in the same manner by locating the frequency shifter 213 immediately before the SHG device 217, as shown in FIG. 8, FIG. 9, or FIG. 10.

Figure 11:
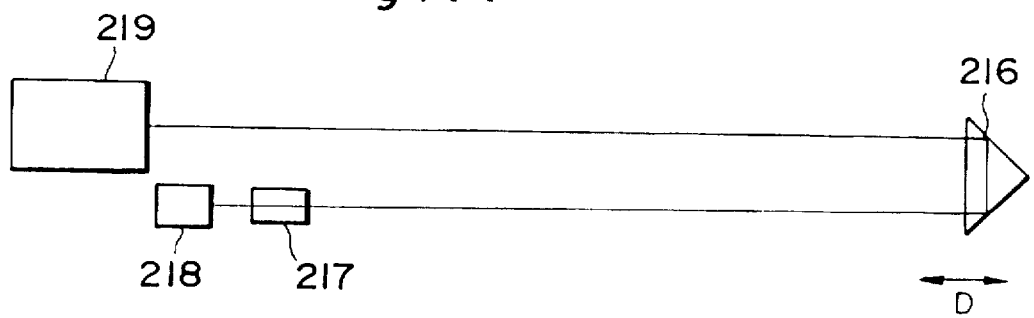
FIG. 11 is a block diagram to show another configuration of the refractive index change measuring apparatus according to the fifth embodiment of the present invention.

The embodiment of FIG. 5 uses the SHG device 212 and frequency shifter 213 to obtain the light beams of the two frequencies, but it is of course possible to use a laser 219 for generating the light of the two frequencies, as shown in FIG. 11.

Figure 12:
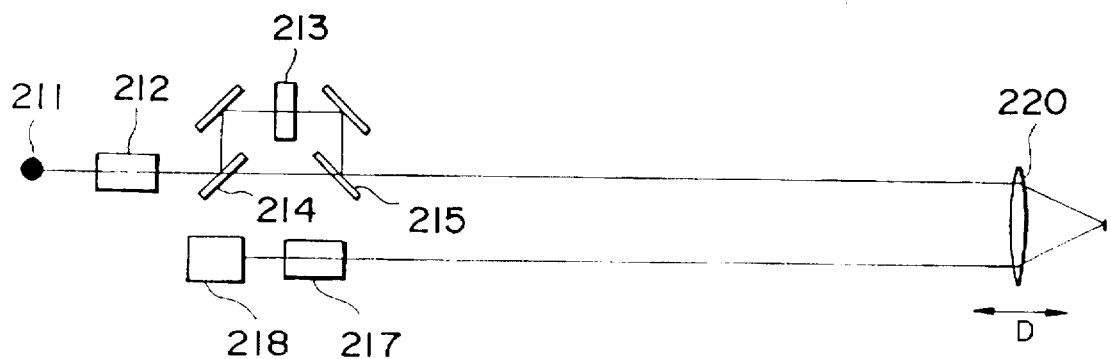
FIG. 12 is a block diagram to show another configuration of the refractive index change measuring apparatus according to the fifth embodiment of the present invention.

As shown in FIG. 12, a cat's-eye 220 moving may be used instead of the moving mirror 216.

Figure 21:
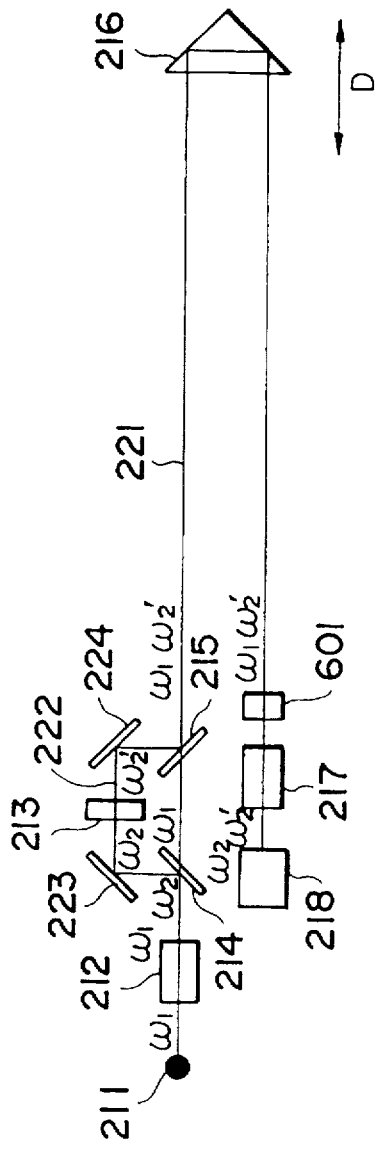
FIG. 21 is an explanatory drawing to show the configuration of the refractive index change measuring apparatus using light wave interference in the third embodiment of the present invention.

The index change measuring apparatus of FIG. 5 may include the direction-of-polarization rotating apparatus 601 for rotating the directions of polarization of the light of frequencies $\omega_1$, $\omega_2$' incident into the SHG device 217 (FIG. 21).

The direction-of-polarization rotating apparatus 601 may be the one shown in FIGS. 19A, 19B or FIGS. 20A, 20B. It is noted that, omitting the casing, the wave plates may be stationarily arranged on the optical path.

The direction-of-polarization rotating apparatus 601 rotates the direction of polarization of the light of frequency $\omega_1$ to a predetermined direction of polarization. This predetermined direction of polarization is a direction of polarization determined by the phase matching conditions of the KTiOPO$_4$ crystal for the SHG device 217. In the present embodiment, the apparatus rotates the direction of polarization of the light of frequency $\omega_1$ to the direction of polarization near 45° relative to the extraordinary direction of the KTiOPO$_4$ crystal. Also, the direction of polarization of the light of frequency $\omega_2$' is rotated to the extraordinary direction of the KTiOPO$_4$ crystal. The method for setting the direction-of-polarization rotating apparatus 601 for rotating the direction of polarization is as already detailed previously.

Since in FIG. 21 the direction-of-polarization rotating apparatus is located before the SHG device 217, the light of frequency $\omega_1$ can be incident in the direction of polarization in which the conversion efficiency of the SHG device 217 into the second harmonic wave is high. Further, the SHG device 217 transmits the light of frequency $\omega_2$', so that the light of frequency $\omega_2$' can be made incident in the direction of polarization in which the second harmonic wave of frequency $\omega_1$ is generated. Thus, the second harmonic wave with high intensity can be generated, and the direction of polarization of the second harmonic wave is matched with that of the light of frequency $\omega_2$'. Therefore, interference light can be obtained with high intensity. Accordingly, the change in the refractive index can be measured with accuracy.

In FIG. 21, the position where the direction-of-polarization rotating apparatus 601 is located is not limited to immediately before the SHG device 217. It may be located closer to the light source 211 than the moving mirror 216 as long as it can rotate the direction of polarization of the incident light into the SHG device 217.

The configurations of FIG. 6 to FIG. 11 may be provided with the direction-of-polarization rotating apparatus in the same manner as in FIG. 21.

The arrangement of FIG. 5 employs a corner cube prism as the moving mirror 216, but a plane mirror may replace it.

The arrangement of FIG. 5 uses the dichroic mirror 214 to separate the light of the two frequencies and then to frequency-shift one light, but the light beams of the two frequencies can be separated by inserting a wave plate and a polarization separating element instead of the dichroic mirror or by using a dispersion prism instead of the dichroic mirror. In addition, when two frequency shifters 213 are connected in series, heterodyne frequency can be set low, which permits the same measurement.

The above light wave interference measuring apparatus can accurately correct errors in distance measurement due to an change in the refractive index of the air and can perform distance measurement with accuracy even if there occurs a local change in the refractive index.

Next explained is a light wave interference measuring apparatus provided with the above direction-of-polarization rotating apparatus 401, 402 in the optical path.

Figure 26:
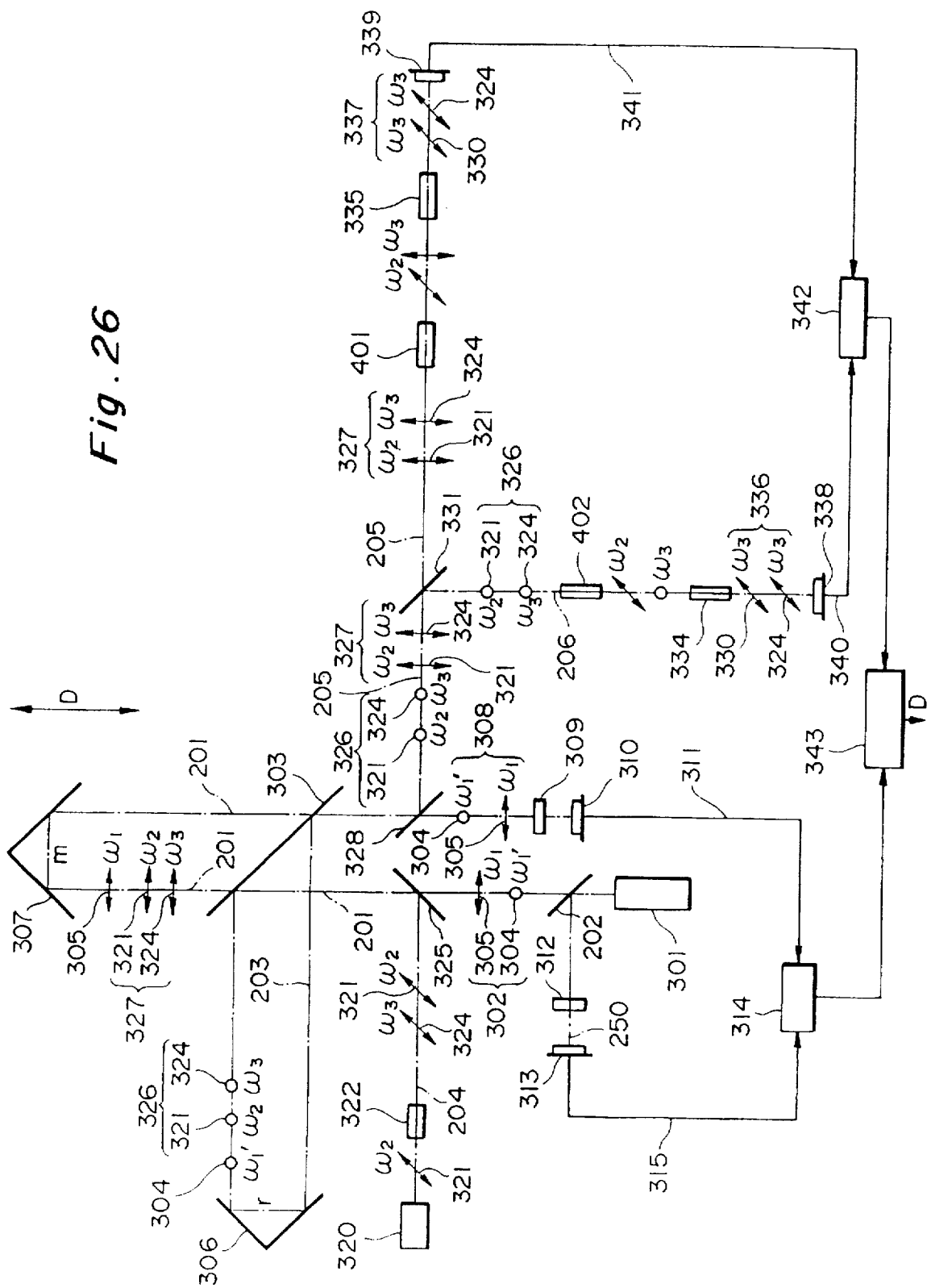
FIG. 26 is an explanatory drawing to show a configuration of the light wave interference measuring apparatus.

First, the configuration of the light wave interference measuring apparatus is explained referring to FIG. 26. The light wave interference measuring apparatus of FIG. 26 is one for monitoring the change in the refractive index of the air by the homodyne interferometry.

Disposed on the optical path 201 in the following order are a light source 301, a beam splitter 202, dichroic mirror 325, a polarization beam splitter 303, a moving mirror 307 a displacement of which is to be measured, an dichroic mirror 328, a polarizer 309, and a photodetector 310. A stationary mirror 306 is disposed on the optical path 203 of light reflected by the polarization beam splitter 303. Further, a polarizer 312 and a photodetector 313 are disposed on the optical path 250 of light reflected by the beam splitter 202. The light source 301 generates light 302 including light 305 of frequency $\omega_1$ and light 304 of frequency $\omega_1$'. Specifically, the light source 301 is a He-Ne laser, and the light 305 is of the wavelength 633 nm. The light 305 and the light 304 have respective frequencies slightly different from each other ($\omega_1' = \omega_1 + \Delta\omega$) and directions of polarization perpendicular to each other. The photodetector 310 and photodetector 313 are connected to a phase meter 314. These compose an optical system for obtaining a displacement $D(\omega_1)$ of the moving mirror 307, measured with the light of frequency $\omega_1$.

Further disposed on the optical path 204 are a light source 320 and a second harmonic generation device (hereinafter referred to as an SHG device) 322. The optical path 204 is coupled with the optical path 201 through the dichroic mirror 325. The light source 320 generates light 321 of frequency $\omega_2$.

The SHG device 322 converts part of the light 321 into light 324 of frequency $\omega_3 = 2\omega_2$. Specifically, the light source 320 is a YAG laser, which generates light of wavelength 1064 nm. The SHG device 322 is formed of the nonlinear optical material KTiOPO$_4$. Further, a polarization beam splitter 331, a direction-of-polarization rotating apparatus 401, an SHG device 335, and a photodetector 339 are disposed on the optical path 205 separated from the optical path 201 by the dichroic mirror 328. A direction-of-polarization rotating apparatus 402, an SHG device 334 and a photodetector 338 are disposed on the optical path 206 separated from the optical path 205 by the polarization beam splitter 331.

The direction-of-polarization rotating apparatus 401, 402 has either one of the arrangements of the above direction-of-polarization rotating apparatus. The SHG devices 334, 335 are made of the same nonlinear optical material KTiOPO$_4$ as the SHG device 322 is.

The photodetectors 338, 339 are connected to a phase meter 342. These constitute together with the polarization beam splitter 303, stationary mirror 306, and moving mirror 307 an optical system for obtaining the phase difference between the displacement $D(\omega_3)$ of the moving mirror 307 measured with the light of frequency $\omega_3$ and the displacement $D(\omega_2)$ of the moving mirror 307 measured with the light of frequency $\omega_2$. This optical system is one for monitoring a change in the refractive index of the air by obtaining $D(\omega_3) - D(\omega_2)$ by the homodyne interferometry.

Next explained is the operation for measuring the true displacement D of the moving mirror 307 as eliminating influence of the change in the refractive index of the air by this apparatus.

First, the light 302, including the light 304 and the light 305 emitted from the light source 301 with the slightly different frequencies and directions of polarization perpendicular to each other, is incident into the polarization beam splitter 303 to be split into the light ($\omega_1$') 304 becoming the reference light and the light ($\omega_1$) 305 becoming the measuring light. The reference light 304 is reflected by the stationary mirror 306 and thereafter is incident again into the polarization beam splitter 303. On the other hand, the measuring light 305 is reflected by the moving mirror 307, which is an object to be measured, and thereafter returns to the polarization beam splitter 303 then to emerge from the polarization beam splitter 303 coaxially with the reference light 304.

The light 308 including the reference light 304 and the measuring light 305, emerging from the polarization beam splitter 303, then passes the polarizer 309. Passing through the polarizer 309, the reference light 304 and measuring light 305 comes to interfere with each other. Information of interference fringes is converted into an electric signal by the photodetector 310. An interference beat signal (frequency $\Delta\omega$) 311 converted into by the photodetector 310, and a reference signal 315 obtained by preliminarily receiving the light immediately after the light source are input into the phase meter 314 to measure a change $\alpha$ of the phase difference of the interference beat signal 311 relative to the phase difference of the reference signal 315 by the heterodyne interferometry. As well known, the displacement $D(\omega_1)$ of the moving mirror 307 can be obtained by calculation with this change in the phase difference $\alpha$ and frequency $\omega_1$.

On the other hand, the light 321 of frequency $\omega_2$ emitted from the light source 320 is incident into the SHG (second harmonic generation) device 322 to produce SHG light 324 of frequency $\omega_3$ (=2 $\omega_2$). Beams of the light 321 and the light 324 are beams of linearly polarized light having directions of polarization making respective angles of 45 degrees relative to the measuring light 305 and reference light 304 as described above. The dichroic mirror 325 couples the two beams of the respective wavelengths, i.e., the light 321 of frequency $\omega_2$ transmitted by the SHG device 322 and the light 324 of frequency $\omega_3$, with the distance-measuring light 302 as described above, and the coupled light is incident into the polarization beam splitter 303. The light 321 and light 324 of the two frequencies incident into the polarization beam splitter 303 is separated into reference light 326 having the same direction of polarization as the reference light 304 and measuring light 327 having the same direction of polarization as the measuring light 305. Each of the reference light 326 and the measuring light 327 includes the light 321 of frequency $\omega_2$ and the light 324 of frequency $\omega_3$. Then the reference light 326 is reflected by the stationary mirror 306, and the measuring light 327 is reflected by the moving mirror 307. After that, they coaxially emerge from the polarization beam splitter 303.

The light including the two frequencies emerging from the polarization beam splitter 303 is separated from the measuring light 308 by the dichroic mirror 328. Further, the polarization beam splitter 331 separates the light 326 including the two frequencies, having passed through the reference optical path, from the light 327 including the two frequencies, having passed through the measuring optical path.

The direction-of-polarization rotating apparatus 402 rotates the direction of polarization of the light 321 of frequency $\omega_2$ included in the reference light 326 to a predetermined direction of polarization. This predetermined direction of polarization is a direction of polarization determined by the phase matching conditions of the KTiOPO$_4$ crystal for the SHG device 334, and in the present embodiment the apparatus rotates it to the direction of polarization near 45° relative to the extraordinary direction of the KTiOPO$_4$ crystal. Also, the apparatus rotates the direction of polarization of the light 324 of frequency $\omega_3$ to the extraordinary direction of the KTiOPO$_4$ crystal for the SHG device 334. The method for setting the direction-of-polarization rotating apparatus 402 for rotating the direction of polarization is as detailed in the first and second embodiments.

Further, the direction-of-polarization rotating apparatus 401 also rotates the direction of polarization of the light 321 of frequency $\omega_2$ included in the measuring light 327 to a predetermined direction of polarization in the same manner. This predetermined direction of polarization is a direction of polarization determined by the phase matching conditions of the KTiOPO$_4$ crystal for the SHG device 335, and in the present embodiment the apparatus rotates the direction of polarization to the direction of polarization near 45° relative to the extraordinary direction of the KTiOPO$_4$ crystal. Further, the apparatus rotates the direction of polarization of the light 324 of frequency $\omega_3$ to the extraordinary direction of the KTiOPO$_4$ crystal for the SHG device 335.

The KTiOPO$_4$ crystal for the SHG devices 334, 335 has such a property that when the light of frequency $\omega_2$ is incident in the direction of polarization determined from the phase matching conditions as described above (near 45° relative to the extraordinary direction), it efficiently generates the second harmonic wave to output it as linearly polarized light parallel to the extraordinary direction of crystal. Further, the KTiOPO$_4$ crystal transmits the light of frequency $\omega_3$ incident in the extraordinary direction of crystal so as to output it in the extraordinary direction of crystal as it is.

Thus, the SHG devices 334, 335 each generate the second harmonic wave of the light 321 of the low frequency $\omega_2$ to emit light 330 of frequency $\omega_3$ (=2$\omega_2$). Since the light 330 of frequency $\omega_3$ has the same direction of polarization (the extraordinary direction of the KTiOPO$_4$ crystal) as the light 324 of the higher frequency $\omega_3$ having passed the SHG device 334, 335, they interfere with each other. The photodetectors 338, 339 receive the interference light 336, 337, respectively. An interference signal 340 from the interference light 336 between the light including the two frequencies having passed through the reference optical path and an interference signal 341 from the interference light 337 between the light including the two frequencies having passed through the measuring optical path are input into the phase meter 342, and a phase difference $\beta$ is detected by measuring a change in the refractive index of the interference signal 341 relative to the phase difference of the interference signal 340. Then $D(\omega_3)-D(\omega_2)$ is obtained by calculation using the phase difference $\beta$ and the frequency $\omega_3$.

Further, an output from the phase meter 314 of the light wave interference measuring apparatus and an output from the phase meter 342 are put into an calculator 343, which executes the following calculation for correcting the change in the refractive of the air to obtain the true displacement D.

$$D=D(\omega_1)-[F(\omega_1)/\{F(\omega_3)-F(\omega_2)\}]\cdot\{D(\omega_3)-D(\omega_2)\} \quad (14)$$

Here, $F(\omega_1)/(F(\omega_3)-F(\omega_2))$ is a constant preliminarily obtained by calculation.

As explained, the light wave interference measuring apparatus can detect the true displacement as corrected for the change in the refractive index, using Eq. 13, by measuring the displacement of the measured object $D(\omega_1)$ and $\{D(\omega_3)-D(\omega_2)\}$, using the light of three frequencies $\omega_1$, $\omega_2$, $\omega_3$.

Since this embodiment is arranged so that the direction-of-polarization rotating apparatus of the first or second embodiment are located before the SHG devices 334, 335, the light 321 of frequency $\omega_2$ can be made incident in the direction of polarization in which the conversion efficiency of SHG device 334, 335 into the second harmonic wave is high. The SHG devices 334, 335 transmit the light 324 of frequency $\omega_3$ so that the light 324 of frequency $\omega_3$ can be made incident in the direction of polarization in which the second harmonic wave of the light 321 of frequency $\omega_2$ is emergent. Thus, the second harmonic wave with high intensity (light 330) can be generated, and interference light with high intensity can be obtained because the directions of polarization of the second harmonic wave (light 330) and the light 324 are coincident with each other. Accordingly, $D(\omega_3)$ $-D(\omega_2)$ can be obtained with accuracy.

It is also possible in the arrangement of this embodiment to remove the casing of the direction-of-polarization rotating apparatus 401, 402 and to locate the wave plates on the optical path.

This embodiment obtained $D(\omega_3)-D(\omega_2)$ utilizing homodyne interferometry, but it may be modified in an arrangement utilizing heterodyne interferometry. Specifically, in FIG. 26, the optical path between the SHG device 322 and the dichroic mirror 325 is branched and an acoustooptic modulator for slightly shifting the frequency is placed in the branched path. This acoustooptic modulator slightly shifts at least either one frequency out of the light 321 of frequency $\omega_2$ and the light 324 of frequency $\omega_3$, and then returns the light into the optical path 204. Utilizing the heterodyne interferometry by such an arrangement, detection is less influenced by an error due to a change in output from the light source 320, and the phase difference can be detected accurately. Accordingly, $D(\omega_3)-D(\omega_2)$ for correction can be accurately detected, which can improve the detection accuracy of the true displacement D.

Figure 27:
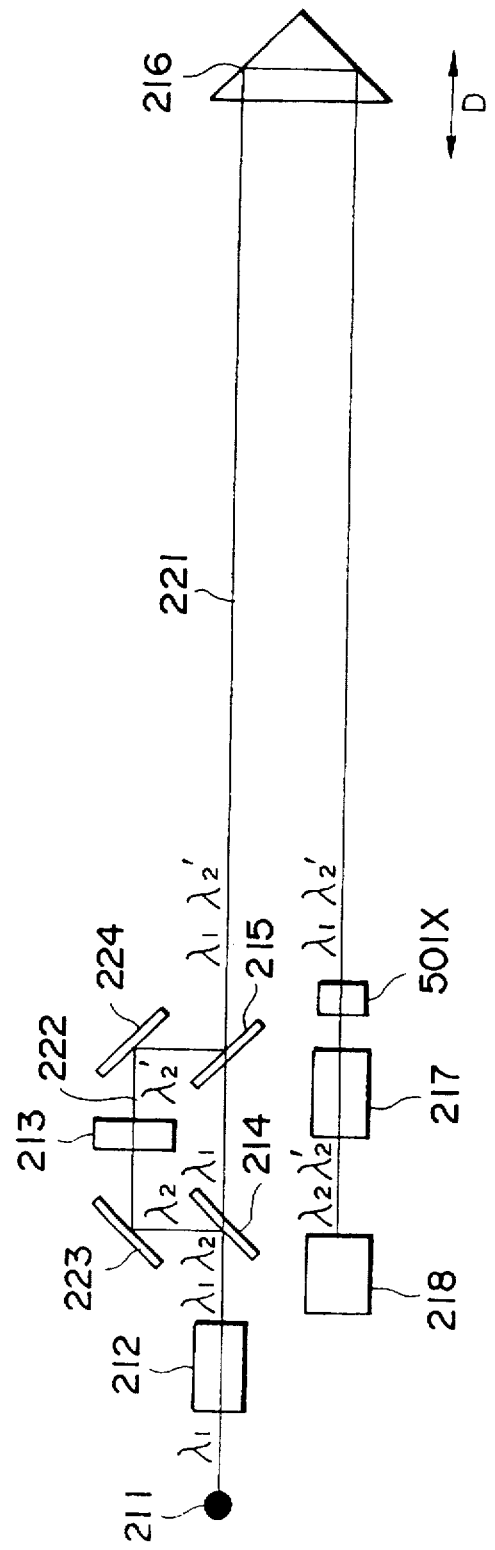
FIG. 27 is an explanatory drawing to show a configuration of a refractive index change monitor.

Next explained referring to FIG. 27 is a refractive index change monitor provided with the above direction-of-polarization rotating apparatus.

The refractive index change monitor of the present embodiment is an apparatus for measuring a change in the refractive index of a space in which a gas such as the air or a liquid is filled. Then disposed on the optical path 221 in a space the index change of which is to be measured are a light source 211, an SHG device 212, an dichroic mirror 214, an dichroic mirror 215, a moving mirror 216, a direction-of-polarization rotating apparatus 501x, an SHG device 217, and a photodetector 218. Further, a mirror 223, a frequency shifter 213, and a mirror 224 are disposed on an optical path 222 of the light reflected by the dichroic mirror 214.

The direction-of-polarization rotating apparatus 501x may be either one of the direction-of-polarization rotating apparatus in the first and second embodiments.

In this structure, the SHG device 212 converts part of the light of wavelength $\lambda_1$ (fundamental wave) emitted from the light source 211 into light of wavelength $\lambda_2$ ($\lambda_2 = (\frac{1}{2}) \cdot \lambda_1$: second harmonic wave). The light of wavelength $\lambda_2$ is reflected by the optical separating element (optical separating element) 214. The frequency shifter 213 shifts the wavelength $\lambda_2$ by a constant value. This yields light of wavelength $\lambda_2'$. The optical coupling element 215 coaxially multiplexes the light of wavelength $\lambda_1$ and the light of wavelength $\lambda_2'$, and the multiplexed light travels in the space the change in the refractive index of which is to be measured, and is then reflected by the moving mirror 216. Further, the multiplexed light is let to travel in the space the change in the refractive index of which is to be measured. Then the direction-of-polarization rotating apparatus 501x rotates the direction of polarization, and the light is made incident into the SHG device 217, which converts the light of wavelength $\lambda_1$ into light of wavelength $\lambda_2$ ($\lambda_2=\frac{1}{2}\cdot\lambda_1$). The light of wavelength $\lambda_2'$ is transmitted by the SHG device 217, so that the light of wavelength $\lambda_2$ may come to interfere with the light of wavelength $\lambda_2'$, thus forming interference fringes. The photodetector 218 detects the phase difference to heterodyne-detect.

This gives, similarly as in the embodiment of FIG. 26, $\{D(\lambda_2')-D(\lambda_1)\}$ corresponding to a difference between measurement results when the displacement of the moving mirror 216 is measured with the two light beams by using the phase difference detected by the photoelectric conversion element (photodetector) 218. (Here, $c=(\omega/(2\pi))\lambda$.) As explained in the third embodiment, $D(\lambda_2')-D(\lambda_1)$ is the value including information of the change in the refractive index of the air. Accordingly, the change in the refractive index of the air can be relatively detected by moving the moving mirror 216 in the constant displacement.

The direction-of-polarization rotating apparatus 501x rotates the direction of polarization of the light of wavelength $\lambda_1$ to a predetermined direction of polarization. This predetermined direction of polarization is the direction of polarization determined by the phase matching conditions of the KTiOPO$_4$ crystal for the SHG device 217, and in the present embodiment the apparatus rotates it to the direction of polarization near 45° relative to the extraordinary direction of the KTiOPO$_4$ crystal. Further, the apparatus rotates the direction of polarization of the light of wavelength $\lambda_2'$ to the extraordinary direction of the KTiOPO$_4$ crystal. The method for setting the direction-of-polarization rotating apparatus 501x for rotating the direction of polarization is as detailed in the embodiments of FIGS. 19A, 19B and FIGS. 20A, 20B.

Since in the present embodiment the direction-of-polarization rotating apparatus of the embodiment of FIGS. 19A, 19B or FIGS. 20A, 20B is located before the SHG device 217, the light of wavelength $\lambda_1$ can be made incident in the direction of polarization in which the conversion efficiency of the SHG device 217 into the second harmonic wave is high. Further, the SHG device 217 transmits the light of wavelength $\lambda_2'$ so that the light of wavelength $\lambda_2'$ can be made incident in the direction of polarization in which the second harmonic wave of wavelength $\lambda_1$ is emergent. Thus, the second harmonic wave with high intensity can be achieved, and interference light with high intensity can be obtained because the directions of polarization of the second harmonic wave and the light of wavelength $\lambda_2'$ are coincident with each other. Accordingly, the change in the refractive index can be monitored with accuracy.

In this embodiment the location of the direction-of-polarization rotating apparatus 501x is not limited to immediately before the SHG device 217, but it may be placed between the moving mirror 216 and the dichroic mirror (optical coupling element) 215.

As described in the above each embodiment, the directions of polarization of light of two frequencies can be rotated to respective, different directions by using the direction-of-polarization rotating apparatus of the first or second embodiment according to the present invention. When this direction-of-polarization rotating apparatus is mounted in the interference optical apparatus provided with the SHG device as in the third or fourth embodiment, the second harmonic wave can be obtained with high intensity and then the interference light can be obtained with high intensity.

As detailed above, the present invention provides the direction-of-polarization rotating apparatus which can rotate the directions of polarization of light of two frequencies to arbitrary directions of polarization independently of each other.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Applications No.335696/1994 filed on Dec. 20, 1994, No.60969/1995 filed on Mar. 20, 1995, No.66469/1995 filed on Mar. 24, 1995 and No.212016/1995 filed on Aug. 21, 1995 are hereby incorporated by reference.

What is claimed is:

1. An apparatus for measuring the refractive index of a medium, having a light source which can emit a light beam and a photodetector arranged in a path way of the light beam, the medium being arranged in said path way, said apparatus comprising:

at least two second harmonic generation devices each of which can convert wavelength of light passing therethrough, said second harmonic generation devices being arranged in said path way; and a unit arranged in said path way and which can rotate a direction of polarization of light passing therethrough, wherein said unit comprises a plurality of wave plates arranged in said path way, and said wave plates being arranged so that said unit rotates the polarization direction of light having first wavelength relative to the polarization direction of light having second wavelength.

2. An apparatus according to claim 1, wherein said unit is arranged in said path way between said second harmonic generation devices.

3. An apparatus according to claim 1, wherein said second harmonic generation devices are comprised of $KTiOPO_4$.

4. An apparatus according to claim 1, wherein said apparatus measures the refractive index of the medium based on a change in an intensity detected by said photodetector.

5. An apparatus according to claim 1, further comprising:

an optical separating element arranged in said path way and which separates the light beam into two components each of which has a different wavelength; and a frequency shifter which can shift the frequency of one of the components separated by said optical separating element, wherein said apparatus measures the refractive index of said medium based on a change in an intensity detected by said photodetector.

6. An apparatus according to claim 1, further comprising:

an optical separating element arranged in said path way and which separates the light beam into two components; and a frequency shifter which can shift the frequency of one of the components separated by said optical separating element, wherein said apparatus measures the refractive index of said medium based on a change in an intensity detected by said photodetector.

7. An apparatus according to claim 1, wherein said unit comprises:

a casing having two windows, each of which is arranged in said path way; and a wave plate arranged in said casing, said wave plate being rotatable.

8. An apparatus according to claim 7, wherein said casing has a slot, and wherein said unit further comprises a handle attached to said wave plate, said handle being movable in said slot.

9. An apparatus according to claim 1, wherein said unit comprises:

a casing having two windows, each of which is arranged in said path way; and a plurality of wave plates arranged in said casing, each of said wave plates being rotatable.

10. An apparatus according to claim 1, wherein said unit comprises a plurality of wave plates arranged in said path way.

11. An apparatus according to claim 1, wherein said unit comprises at least three wave plates arranged in said path way.

12. An apparatus according to claim 1, wherein said unit rotates said polarization directions of the respective lights having first and second wavelengths independently.

13. An apparatus according to claim 1, wherein said unit comprises wave plates arranged in said path way, and wherein said unit can rotate the polarization direction of light passing therethrough independently of wavelength.

14. An apparatus according to claim 1, wherein said apparatus is an apparatus for measuring a change in the refractive index of the medium.

15. An apparatus according to claim 1, further comprising:

a first beam splitter arranged in said path way, said first beam splitter dividing said light beam into two components after said light beam has passed through one of said second harmonic generation devices;

first and second mirrors, each of which is arranged to oppose said first beam splitter, said first mirror reflecting one of the components divided by said first beam splitter, the medium being arranged between said first mirror and said first beam splitter, said second mirror reflecting the other of the components divided by said first beam splitter back toward said first beam splitter, the respective components, having been reflected by said first and second mirrors and having arrived at said first beam splitter, being coupled by said first beam splitter, the coupled light beam continuing to travel on said path way;

a second beam splitter arranged in said path way between said first beam splitter and another of said second harmonic generation devices, the coupled light beam being again divided into two components by said second beam splitter, one of the components divided by said second beam splitter being detected by said photodetector; and another photodetector arranged to detect the other of the components divided by said second beam splitter.

16. An apparatus according to claim 1, further comprising:

a beam splitter arranged in said path way, said beam splitter dividing said light beam into two components after said light beam has passed through one of said second harmonic generation devices, wherein one of the components divided by said beam splitter is detected by said photodetector; and another photodetector arranged to detect the other of the components divided by said beam splitter.

17. An apparatus for measuring the refractive index of a medium, having a light source which can emit a light beam and a photodetector arranged in a path way of the light beam, the medium being arranged in said path way, said apparatus comprising:

at least two second harmonic generation devices each of which can convert wavelength of light passing therethrough, said second harmonic generation devices being arranged in said path way; and a unit arranged in said path way and which can rotate a direction of polarization of light passing therethrough, wherein said unit comprises:

a first wave plate having a retardation $(2n-1)\pi/2$ for light having a first wavelength and a retardation $(2m-1)\pi$ for light having a second wavelength;

a second wave plate having a retardation $(2p-1)\pi/2$ for light having a first wavelength and a retardation $(2q-1)\pi$ for light having a second wavelength;

a third wave plate having a retardation $(2r-1)\pi$ for light having a first wavelength and a retardation $2s\pi$ for light having a second wavelength, wherein said wave plates are arranged on a common axis, and wherein n, m, p, q, r, s are integers.

18. An apparatus for measuring the refractive index of a medium, having a light source which can emit a light beam and a photodetector arranged in a path way of the light beam, the medium being arranged in said path way, said apparatus comprising:

at least two second harmonic generation devices each of which can convert wavelength of light passing therethrough, said second harmonic generation devices being arranged in said path way; and a unit arranged in said path way and which can rotate a direction of polarization of light passing therethrough, wherein said unit comprises:

a first wave plate having a retardation $(2n-1)\pi$ for light having a first wavelength and light having a second wavelength; and a second wave plate having a retardation $(2m-1)\pi$ for light having a first wavelength and a retardation $2p\pi$ for light having a second wavelength, wherein said wave plates are arranged on a common axis, and wherein n, m, p are integers.

19. A displacement measuring system comprising said apparatus of claim 1.

20. A direction-of-polarization rotating unit comprising:

first wave plate having a retardation $(2n-1)\pi/2$ for light having a first wavelength and a retardation $(2m-1)\pi$ for light having a second wavelength;

a second wave plate having a retardation $(2p-1)\pi/2$ for light having the first wavelength and a retardation $(2q-1)\pi$ for light having the second wavelength; and a third wave plate having a retardation $(2r-1)\pi$ for light having the first wavelength and a retardation $2s\pi$ for light having the second wavelength, wherein said wave plates are arranged on a common axis, and wherein n, m, p, q, r, s are integers.

21. A direction-of-polarization rotating unit comprising:

a first wave plate having a retardation $(2n-1)\pi$ for light having a first wavelength and light having a second wavelength; and a second wave plate having a retardation $(2m-1)\pi$ for light having the first wavelength and a retardation $2p\pi$ for light having the second wavelength, wherein said wave plates are arranged on a common axis, and wherein n, m, p are integers.

22. An apparatus for measuring the refractive index of a medium, having a light source which can emit a light beam and a photodetector arranged in a path way of the light beam, the medium being arranged in said path way, said apparatus comprising:

at least two second harmonic generation devices each of which can convert wavelength of light passing therethrough, said second harmonic generation devices being arranged in said path way; and a unit arranged in said path way and which can rotate a direction of polarization of light passing therethrough, wherein said unit comprises a plurality of wave plates arranged in said path way, and said wave plates being arranged so that said unit rotates the polarization direction of light having first wavelength and does not rotate the polarization direction of light having second wavelength.

* * * * *

UNITED STATES PATENT AND TRADEMARK OFFICE
CERTIFICATE OF CORRECTION

PATENT NO.  :  5,767,971

DATED       :  June 16, 1998

INVENTOR(S) :  Hitoshi KAWAI, Jun KAWAKAMI, Akira ISHIDA, Kouichi TSUKIHARA

It is certified that error appears in the above-identified patent and that said Letters Patent is hereby corrected as shown below:

Title page:

item [30] Foreign Application Priority Data, line 1, change "Dec. 30, 1994" to "Dec. 20, 1994."

Signed and Sealed this

Twenty-second Day of September, 1998

Attest:

BRUCE LEHMAN

Attesting Officer

Commissioner of Patents and Trademarks